(12) United States Patent
Yagi et al.

(10) Patent No.: US 8,481,759 B2
(45) Date of Patent: Jul. 9, 2013

(54) PROCESS FOR PRODUCING WINE LACTONE

(75) Inventors: Kenji Yagi, Kanagawa (JP); Yasuhiro Komatsuki, Kanagawa (JP); Hideo Ujihara, Kanagawa (JP); Kenya Ishida, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 13/483,373

(22) Filed: May 30, 2012

(65) Prior Publication Data

US 2013/0030193 A1    Jan. 31, 2013

(30) Foreign Application Priority Data

Jun. 1, 2011    (JP) .................................. 2011-123267

(51) Int. Cl.
*C07D 305/12*    (2006.01)
(52) U.S. Cl.
USPC ......................................................... 549/307
(58) Field of Classification Search
USPC ......................................................... 549/307
See application file for complete search history.

(56) References Cited

U.S. PATENT DOCUMENTS 5,420,306 A    5/1995    Noyori et al.

FOREIGN PATENT DOCUMENTS

| JP | 04-108782 A | 4/1992 |
|---|---|---|
| JP | 2004-269463 A | 9/2004 |
| JP | 2010-195765 A | 9/2010 |
| JP | 2011-246435 A | 12/2011 |
| JP | 2012-067071 A | 4/2012 |
| WO | WO 2011/135753 A1 | 11/2011 |
| WO | WO 2012/026201 A1 | 3/2012 |

OTHER PUBLICATIONS

Guth et al. Helvetica Chmica Acta 1996, 79, 1559-1571.*
Bartlett et al., "Evaluation of the Claisen Rearrangement of 2-Cyclohexenols for the Stereoselective Construction of a Terpene Synthon," J. Org. Chem., 1981, 46:3896-3900.
Bergner et al., "Synthesis of Enantiomerically Pure (−)—Wine Lactone Based on a Palladium-Catalyzed Enantioselective Allylic Substitution," Eur. J. Org. Chem., 2000, 419-423.
Bishop et al., "Synthesis and Characterization of Monothiosuccinimides," J. Org. Chem., 1989, 54:1876-1883.
Chavan et al., "An efficient and simple synthesis of (−)—wine lactone," Tetrahedron: Asymmetry, 2001, 12:2985-2988.
Guth, Helmut, "Determination of the Configuration of Wine Lactone," Helvetica Chimica Acta, 1996, 79:1559-1571.
Kreiser et al., "Zur Regioselektivitat Beim Aldol-Ringschluss," Tetrahedron Letters, 1981, 22(5):429-432, with English summary on first page.
Moreno-Dorado et al., "An Easy Route to 11-Hydroxy-eudesmanolides. Synthesis of (±) Decipienin A.,"Tetrahedron, 1999, 55(22):6997-7010.
Shi et al., "OSW Saponins: Facile Synthesis toward a New Type of Structures with Potent Antitumor Activities," J. Org. Chem., 2005, 70(25):10354-10367.

* cited by examiner

*Primary Examiner* — Nizal Chandrakumar
(74) *Attorney, Agent, or Firm* — Foley & Lardner LLP

(57) ABSTRACT

The present invention relates to a method comprising (A) reacting a β-keto ester with a 2-halo ester under basic conditions to obtain a 2-aceto-3-methyl-succinic acid ester; (B) reacting the resulting 2-aceto-3-methyl-succinic acid ester with methyl vinyl ketone under basic conditions, optionally followed by a decarboxylation reaction and hydrolysis, etc., to obtain an α-methyl-γ-keto acid; and (C) reducing the resulting α-methyl-γ-keto acid to obtain wine lactone or a stereoisomer thereof or a mixture thereof. Alternatively, the present invention relates to a method comprising step (A) as recited above; (B) reacting the resulting 2-aceto-3-methyl-succinic acid ester with methyl vinyl ketone under basic conditions, followed by decarboxylation reaction to obtain an α-methyl-γ-keto acid ester; and (E) reducing the resulting α-methyl-γ-keto acid ester in the presence of a ruthenium complex having a specific structure and in the presence of a hydrogen donor to obtain wine lactone or a stereoisomer thereof or a mixture thereof.

21 Claims, No Drawings

PROCESS FOR PRODUCING WINE LACTONE

TECHNICAL FIELD

The present invention relates to a process for producing wine lactone, which is useful as a flavor or fragrance compound, or a stereoisomer thereof or a mixture thereof.

BACKGROUND ART

Wine lactone, whose chemical name is (3a,4,5,7a)-tetrahydro-3,6-dimethyl-benzofuran-2(3H)-one, was found in 1975 by Southwell from metabolites in koalas. This compound was isolated from white wine in 1996 by Guth as being one of the most important aroma components of white wine and thus named as "wine lactone." Wine lactone has eight types of stereoisomers, all of which were synthesized by Guth, and the compound naturally occurring (i.e., wine lactone) is a (3S, 3aS,7aR) isomer. Among the eight types of stereoisomers, this (3S,3aS,7aR) isomer was found to have the strongest aroma and to be excellent in the quality of aroma (Non-patent Document 1: Helv. Chim. Acta, 79, (1996), 1559-1571).

There are various reports of how to produce wine lactone.

For example, Non-patent Document 1 (supra) reports a process for producing all stereoisomers including wine lactone, a process mediated by Diels-Alder reaction for 6-membered ring formation, and a process starting from limonene having the same stereochemistry as the 3a-position of wine lactone. However, the process for producing all stereoisomers is not cost-effective because wine lactone, i.e., the (3S,3aS, 7aR) isomer which is excellent in aroma and the quality thereof is obtained in a yield as low as 20%. The process mediated by Diels-Alder reaction allows diastereoselective synthesis of a desired stereoisomer, but is not suitable for use on an industrial scale because of using harmful reagents, such as chromic acid for oxidation reaction and methyl iodide for methylation. The process starting from limonene is also difficult to use on an industrial scale because of using harmful reagents, such as chromic acid for oxidation reaction.

Non-patent Document 2 (J. Org. Chem., 46 (1981), 3896-3900) reports a process for obtaining wine lactone from a 2-cyclohexenol derivative through Claisen rearrangement reaction. According to this process, it is possible to synthesize wine lactone in a diastereoselective manner, but this process is not suitable for use on an industrial scale because of great difficulty in obtaining the starting 2-cyclohexenol derivative and because of using harmful reagents, such as methyl iodide for methylation.

Non-patent Document 3 (Eur. J. Org. Chem., (2000), 419-423) describes a process for obtaining wine lactone in a stereoselective manner through addition reaction of a malonic acid ester using a palladium complex as a catalyst. According to this process, it is possible to obtain only the (3S,3aS,7aR) isomer in a stereoselective manner. However, this process requires the stages of lactonization, lactone opening and recyclization, and hence involves a larger number of steps and complicated procedures. Moreover, this process is not suitable for use on an industrial scale because of using harmful reagents, such as methyl iodide for methylation.

Non-patent Document 4 (Tetrahedron: Asymmetry, 12, (2001), 2985-2988) discloses a process involving hydration of isolimonene and synthesis of a carboxylic acid through oxidation reaction, followed by ring closure reaction to synthesize wine lactone. According to this process, it is possible to synthesize a desired stereoisomer in a diastereoselective manner. However, this process is not suitable for use on an industrial scale because of using harmful reagents, such as chromic acid for oxidation reaction.

Patent Document 1 (JP 2004-269463 A) describes a process starting from a β-keto ester, which involves reduction of carbonyl groups using an optically active oxazaborolidine as an chiral ligand, followed by hydrolysis and cyclization reaction to synthesize wine lactone. However, this process also has a problem in using harmful reagents, such as butyl lithium and methyl iodide for methylation.

Patent Document 2 (JP 2010-195765 A) describes a process for obtaining wine lactone by simultaneous formation of two rings through Diels-Alder reaction. This process is advantageous in that wine lactone can be synthesized without using any harmful reagents, but it cannot be regarded as an industrially advantageous process because the temperature required for cyclization reaction is as very high as 200° C.

PRIOR ART DOCUMENTS

Patent Documents
Patent Document 1: JP 2004-269463 A
Patent Document 2: JP 2010-195765 A
Non-Patent Documents
Non-patent Document 1: Helv. Chim. Acta, 79, (1996), 1559-1571
Non-patent Document 2: J. Org. Chem., 46 (1981), 3896-3900
Non-patent Document 3: Eur. J. Org. Chem., (2000), 419-423
Non-patent Document 4: Tetrahedron: Asymmetry, 12, (2001), 2985-2988
Non-patent Document 5: J. Org. Chem. 54, 1876-1883 (1989)

SUMMARY OF THE INVENTION

Problem to be Solved by the Invention

Under the circumstances as stated above, there is a demand for the provision of a simple process for producing wine lactone or a stereoisomer thereof without using any harmful or expensive reagents and without requiring any extreme reaction conditions such as extremely low or high temperatures.

Means to Solve the Problem

As a result of extensive and intensive efforts made to solve the problems stated above, the inventors of the present invention have found that wine lactone or a stereoisomer thereof or a mixture thereof can be produced through fewer steps without using any harmful or expensive reagents. Moreover, the inventors have also found that wine lactone and a diastereomeric isomer thereof can be produced in a highly selective manner, as needed. These findings led to the completion of the present invention.

Namely, the present invention relates to a process for producing wine lactone or a stereoisomer thereof or a mixture thereof, as shown below.

[1] A process for producing a compound represented by formula (a), which is wine lactone or a stereoisomer thereof or a mixture thereof:

[Formula 1]

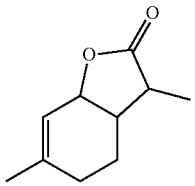
(a)

wherein said process comprises:

A) the step of reacting a β-keto ester represented by formula (1):

[Formula 2]

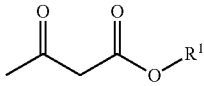
(1)

[wherein $R^1$ is an alkyl group containing 1 to 4 carbon atoms]

with a 2-halo ester represented by formula (2):

[Formula 3]

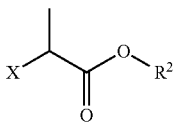
(2)

[wherein $R^2$ is an alkyl group containing 1 to 4 carbon atoms, and X is a chlorine atom or a bromine atom]

under basic conditions to obtain a 2-aceto-3-methyl-succinic acid ester represented by formula (3):

[Formula 4]

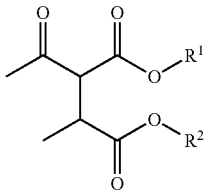
(3)

[wherein $R^1$ is as defined in formula (1), and $R^2$ is as defined in formula (2)];

B-1) the step of reacting the 2-aceto-3-methyl-succinic acid ester obtained in step A) with methyl vinyl ketone under basic conditions, followed by hydrolysis to obtain an α-methyl-γ-keto acid represented by formula (4):

[Formula 5]

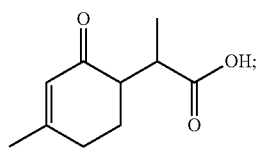
(4)

and

C) the step of reducing the α-methyl-γ-keto acid obtained in step B-1) to obtain the compound represented by formula (a).

[2] A process for producing a compound represented by formula (a), which is wine lactone or a stereoisomer thereof or a mixture thereof:

[Formula 6]

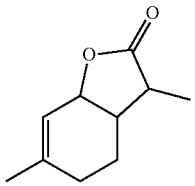
(a)

wherein said process comprises:

A) the step of reacting a β-keto ester represented by formula (1):

[Formula 7]

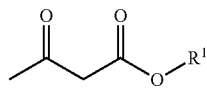
(1)

[wherein $R^1$ is an alkyl group containing 1 to 4 carbon atoms]

with a 2-halo ester represented by formula (2):

[Formula 8]

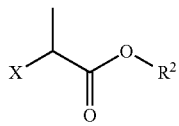
(2)

[wherein $R^2$ is an alkyl group containing 1 to 4 carbon atoms, and X is a chlorine atom or a bromine atom]

under basic conditions to obtain a 2-aceto-3-methyl-succinic acid ester represented by formula (3):

[Formula 9]

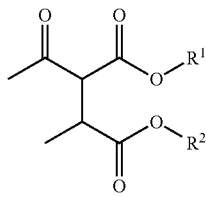

(3)

[wherein $R^1$ is as defined in formula (1), and $R^2$ is as defined in formula (2)];

B-2) the step of reacting the 2-aceto-3-methyl-succinic acid ester obtained in step A) with methyl vinyl ketone under basic conditions, followed by decarboxylation reaction to obtain an α-methyl-γ-keto acid ester represented by formula (5):

[Formula 10]

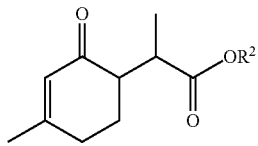

(5)

[wherein $R^2$ is as defined in formula (2)];

B-3) the step of hydrolyzing the α-methyl-γ-keto acid ester obtained in step B-2) to obtain an α-methyl-γ-keto acid represented by formula (4):

[Formula 11]

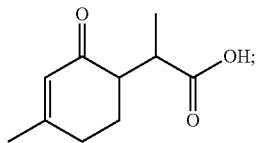

(4)

and

C) the step of reducing the α-methyl-γ-keto acid obtained in step B-3) to obtain the compound represented by formula (a).

[3] The process according to [1] or [2] above, wherein step C) comprises causing asymmetric reduction reaction in the presence of an optically active form of a ruthenium complex selected from compounds represented by formula (6) or (7) and in the presence of a hydrogen donor:

[Formula 12]

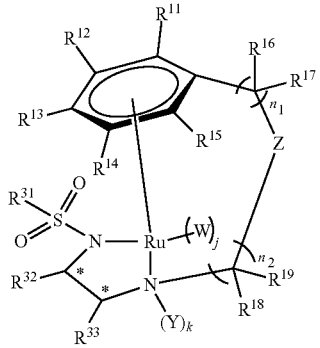

(6)

[wherein * represents an asymmetric carbon atom, $R^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—$NR^{20}R^{21}$), a 5- or 6-membered cyclic amino group, an acylamino group (—NH—CO—$R^{20}$), a hydroxyl group, an alkoxy group (—$OR^{20}$), an acyl group (—CO—$R^{20}$), a carboxyl group, an alkoxycarbonyl group (—$COOR^{20}$), a phenoxycarbonyl group, a mercapto group, an alkylthio group (—$SR^{20}$), a silyl group (—$SiR^{20}R^{21}R^{22}$) and a nitro group (—$NO_2$), wherein $R^{20}$, $R^{21}$ and $R^{22}$ are each independently a hydrogen atom, an alkyl group containing 1 to 10 carbon atoms, or a cycloalkyl group containing 3 to 10 carbon atoms, Y is a hydrogen atom, W is a trifluoromethanesulfonyloxy group, a p-toluenesulfonyloxy group, a methanesulfonyloxy group, a benzenesulfonyloxy group, a hydrogen atom, or a halogen atom, j and k are each independently 0 or 1, provided that j+k is not 1, $R^{32}$ and $R^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, $R^{32}$ and $R^{33}$ may together form a ring, $R^{11}$, $R^{12}$, $R^{13}$, $R^{14}$ and $R^{15}$ each independently represent a hydrogen atom, an alkyl group containing 1 to 10 carbon atoms, or an alkoxy group containing 1 to 10 carbon atoms, $R^{16}$, $R^{17}$, $R^{18}$ and $R^{19}$ are each independently a hydrogen atom, a hydroxyl group, an alkyl group containing 1 to 10 carbon atoms, or an alkoxy group containing 1 to 10 carbon atoms, or alternatively, $R^{16}$ and $R^{17}$ may form a carbonyl group together with their adjacent carbon atom and/or $R^{18}$ and $R^{19}$ may form a carbonyl group together with their adjacent carbon atom, Z is an oxygen atom or a sulfur atom, $n_1$ is 1 or 2, and $n_2$ is an integer of 1 to 3]

[Formula 13]

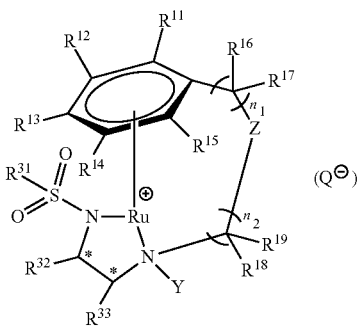

(7)

$(Q^\ominus)$

[wherein * represents an asymmetric carbon atom, $R^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—$NR^{20}R^{21}$) a 5- or 6-membered cyclic amino group, an acylamino group (—NH—CO—$R^{20}$), a hydroxyl group, an alkoxy group (—$OR^{20}$), an acyl group (—CO—$R^{20}$), a carboxyl group, an alkoxycarbonyl group (—$COOR^{20}$), a phenoxycarbonyl group, a mercapto group, an alkylthio group (—$SR^{20}$), a silyl group (—$SiR^{20}R^{21}R^{22}$) and a nitro group (—$NO_2$), $R^{20}$, $R^{21}$ and $R^{22}$ are each independently a hydrogen atom, an alkyl group containing 1 to 10 carbon atoms, or a cycloalkyl group containing 3 to 10 carbon atoms, Y is a hydrogen atom, $R^{32}$ and $R^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, $R^{32}$ and $R^{33}$ may together form a ring, $R^{11}$, $R^{12}$, $R^{13}$, $R^{14}$ and $R^{15}$ are each independently a hydrogen atom, an alkyl group containing 1 to 10 carbon atoms, or an alkoxy group containing 1 to 10 carbon atoms, $R^{16}$, $R^{17}$, $R^{18}$ and $R^{19}$ are each independently a hydrogen atom, a hydroxyl group, an alkyl group containing 1 to 10 carbon atoms, or an alkoxy group containing 1 to 10 carbon atoms, or alternatively, $R^{16}$ and $R^{17}$ may form a carbonyl group together with their adjacent carbon atom and/or $R^{18}$ and $R^{19}$ may form a carbonyl group together with their adjacent carbon atom, Z is an oxygen atom or a sulfur atom, $Q^-$ is a counter anion, $n_1$ is 1 or 2, and $n_2$ is an integer of 1 to 3].

[4] The process according to [3] above, wherein the ruthenium complex represented by formula (6) is a compound represented by the following formula:

[Formula 14]

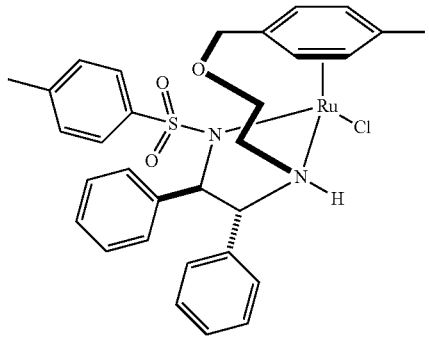

[5] The process according to [1] or [2] above, which further comprises the step of distilling the compound obtained in step C) under basic conditions to obtain a diastereomeric isomer mixture composed of (3S,3aS,7aR) and (3R,3aR,7aS) isomers represented by the following formulae:

[Formula 15]

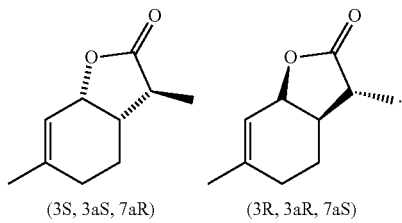

(3S, 3aS, 7aR)     (3R, 3aR, 7aS)

[6] The process according to [5] above, wherein the content of the diastereomeric isomer mixture composed of (3S,3aS,7aR) and (3R,3aR,7aS) isomers is 90% by weight or more, relative to the total weight of the compound represented by formula (a).

[7] The process according to [3] or [4] above, which further comprises the step of distilling the compound obtained in step C) under basic conditions to obtain a diastereomeric isomer mixture composed of (3S,3aS,7aR) and (3R,3aR, 7aS) isomers represented by the following formulae:

[Formula 16]

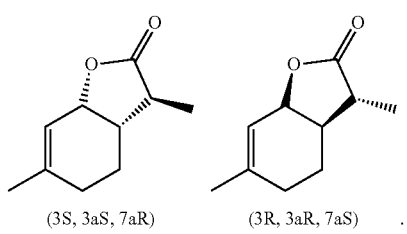

(3S, 3aS, 7aR)     (3R, 3aR, 7aS)

[8] The process according to [7] above, which further comprises the step of recrystallization to obtain the (3S,3aS, 7aR) isomer represented by the following formula:

[Formula 17]

(3S, 3aS, 7aR)

[9] A process for producing a compound represented by formula (a), which is wine lactone or a stereoisomer thereof or a mixture thereof:

[Formula 18]

(a)

wherein said process comprises:

A) the step of reacting a β-keto ester represented by formula (1):

[Formula 19]

(1)

[wherein R¹ is an alkyl group containing 1 to 4 carbon atoms]

with a 2-halo ester represented by formula (2):

[Formula 20]

(2)

[wherein R² is an alkyl group containing 1 to 4 carbon atoms, and X is a chlorine atom or a bromine atom]

under basic conditions to obtain a 2-aceto-3-methyl-succinic acid ester represented by formula (3):

[Formula 21]

(3)

[wherein R¹ is as defined in formula (1), and R² is as defined in formula (2)];

B-2) the step of reacting the 2-aceto-3-methyl-succinic acid ester obtained in step A) with methyl vinyl ketone under basic conditions, followed by decarboxylation reaction to obtain an α-methyl-γ-keto acid ester represented by formula (5):

[Formula 22]

(5)

[wherein R² is as defined in formula (2)]; and

E) the step of reducing the α-methyl-γ-keto acid ester obtained in step B-2) in the presence of a ruthenium complex selected from compounds represented by formula (6) or (7) and in the presence of a hydrogen donor to obtain the compound represented by formula (a):

[Formula 23]

(6)

[wherein * represents an asymmetric carbon atom,
R³¹ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—NR²⁰R²¹), a 5- or 6-membered cyclic amino group, an acylamino group (—NH—CO—R²⁰), a hydroxyl group, an alkoxy group (—OR²⁰), an acyl group (—CO—R²⁰), a carboxyl group, an alkoxycarbonyl group (—COOR$^{20}$), a phenoxycarbonyl group, a mercapto group, an alkylthio group (—SR$^{20}$), a silyl group (—SiR$^{20}$R$^{21}$R$^{22}$) and a nitro group (—NO$_2$), wherein R$^{20}$, R$^{21}$ and R$^{22}$ are each independently a hydrogen atom, an alkyl group containing 1 to 10 carbon atoms, or a cycloalkyl group containing 3 to 10 carbon atoms, Y is a hydrogen atom, W is a trifluoromethanesulfonyloxy group, a p-toluenesulfonyloxy group, a methanesulfonyloxy group, a benzenesulfonyloxy group, a hydrogen atom, or a halogen atom, j and k are each independently 0 or 1, provided that j+k is not 1, R$^{32}$ and R$^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, R$^{32}$ and R$^{33}$ may together form a ring, R$^{11}$, R$^{12}$, R$^{13}$, R$^{14}$ and R$^{15}$ each independently represent a hydrogen atom, an alkyl group containing 1 to 10 carbon atoms, or an alkoxy group containing 1 to 10 carbon atoms, R$^{16}$, R$^{17}$, R$^{18}$ and R$^{19}$ are each independently a hydrogen atom, a hydroxyl group, an alkyl group containing 1 to 10 carbon atoms, or an alkoxy group containing 1 to 10 carbon atoms, or alternatively, R$^{16}$ and R$^{17}$ may form a carbonyl group together with their adjacent carbon atom and/or R$^{18}$ and R$^{19}$ may form a carbonyl group together with their adjacent carbon atom, Z is an oxygen atom or a sulfur atom, $n_1$ is 1 or 2, and $n_2$ is an integer of 1 to 3]

[Formula 24]

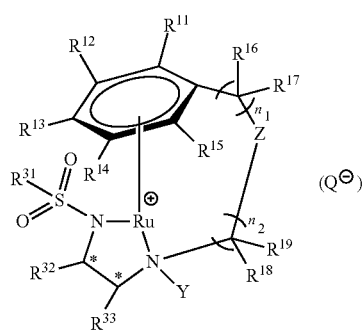

(7)

[wherein * represents an asymmetric carbon atom,

R$^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—NR$^{20}$R$^{21}$) a 5- or 6-membered cyclic amino group, an acylamino group (—NH—CO—R$^{20}$), a hydroxyl group, an alkoxy group (—OR$^{20}$), an acyl group (—CO—R$^{20}$), a carboxyl group, an alkoxycarbonyl group (—COOR$^{20}$), a phenoxycarbonyl group, a mercapto group, an alkylthio group (—SR$^{20}$), a silyl group (—SiR$^{20}$R$^{21}$, R$^{22}$) and a nitro group (—NO$_2$), R$^{20}$, R$^{21}$ and R$^{22}$ are each independently a hydrogen atom, an alkyl group containing 1 to 10 carbon atoms, or a cycloalkyl group containing 3 to 10 carbon atoms, Y is a hydrogen atom, R$^{32}$ and R$^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, R$^{32}$ and R$^{33}$ may together form a ring, R$^{11}$, R$^{12}$, R$^{13}$, R$^{14}$ and R$^{15}$ are each independently a hydrogen atom, an alkyl group containing 1 to 10 carbon atoms, or an alkoxy group containing 1 to 10 carbon atoms, R$^{16}$, R$^{17}$, R$^{18}$ and R$^{19}$ are each independently a hydrogen atom, a hydroxyl group, an alkyl group containing 1 to 10 carbon atoms, or an alkoxy group containing 1 to 10 carbon atoms, or alternatively, R$^{16}$ and R$^{17}$ may form a carbonyl group together with their adjacent carbon atom and/or R$^{18}$ and R$^{19}$ may form a carbonyl group together with their adjacent carbon atom, Z is an oxygen atom or a sulfur atom, Q$^-$ is a counter anion, $n_1$ is 1 or 2, and $n_2$ is an integer of 1 to 3].

[10] The process according to [9] above, wherein in step E), the ruthenium complex selected from compounds represented by formula (6) or (7) is an optically active ruthenium complex and is used to cause asymmetric reduction reaction.

[11] The process according to [9] or [10] above, wherein the ruthenium complex represented by formula (6) is a compound represented by the following formula:

[Formula 25]

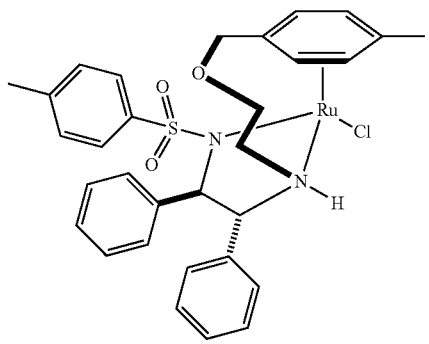

[12] A process for producing a compound represented by formula (a), which is wine lactone or a stereoisomer thereof or a mixture thereof:

[Formula 26]

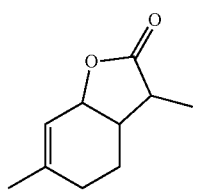

(a)

wherein said process comprises:

A) the step of reacting a β-keto ester represented by formula (1):

[Formula 27]

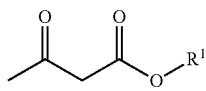
(1)

[wherein $R^1$ is an alkyl group containing 1 to 4 carbon atoms] with a 2-halo ester represented by formula (2):

[Formula 28]

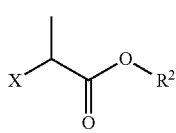
(2)

[wherein $R^2$ is an alkyl group containing 1 to 4 carbon atoms, and X is a chlorine atom or a bromine atom] under basic conditions to obtain a 2-aceto-3-methyl-succinic acid ester represented by formula (3):

[Formula 29]

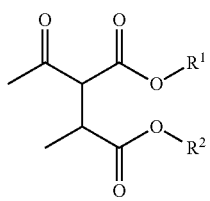
(3)

[wherein $R^1$ is as defined in formula (1), and $R^2$ is as defined in formula (2)];

B-2) the step of reacting the 2-aceto-3-methyl-succinic acid ester obtained in step A) with methyl vinyl ketone under basic conditions, followed by decarboxylation reaction to obtain an α-methyl-γ-keto acid ester represented by formula (5):

[Formula 30]

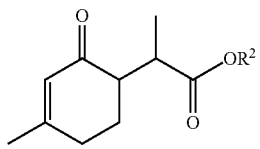
(5)

[wherein $R^2$ is as defined in formula (2)]; and

E) the step of subjecting the α-methyl-γ-keto acid ester obtained in step B-2) to asymmetric hydrogenation reaction under basic conditions and in the presence of an optically active ruthenium complex represented by formula (8) and a hydrogen gas to obtain the compound represented by formula (a):

[Formula 31]

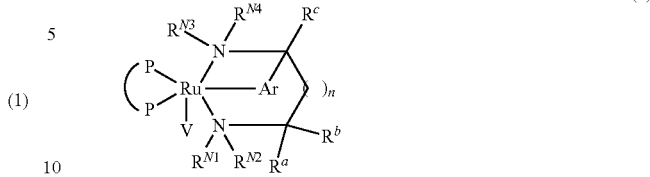
(8)

[wherein P⌒P represents an optically active diphosphine,

V is an anionic group, $R^a$, $R^b$ and $R^c$ are each independently a hydrogen atom, an optionally substituted $C_1$ to $C_{20}$ alkyl group, an optionally substituted $C_2$ to $C_{20}$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclyl group, or alternatively, $R^b$ and $R^c$ may together form an alkylene group or an alkylenedioxy group, $R^{N1}$, $R^{N2}$, $R^{N3}$ and $R^{N4}$ are each independently a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$ and $R^{N4}$ is a hydrogen atom, and $R^{N1}$ and $R^a$ may together form an alkylene group, n is an integer of 0 to 3, and Ar is an optionally substituted arylene group].

[13] The process according to [12] above, wherein the optically active ruthenium complex of formula (8) is a compound represented by the following formula:

[Formula 32]

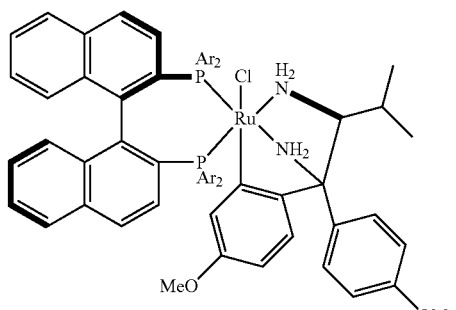

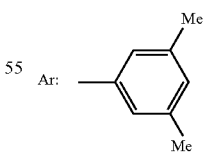

[wherein Me represents a methyl group].

[14] The process according to any one of [9] to [13] above, which further comprises the step of distilling the compound obtained in step E) under basic conditions to obtain a diastereomeric isomer mixture composed of (3S,3aS, 7aR) and (3R,3aR,7aS) isomers represented by the following formulae:

[Formula 33]

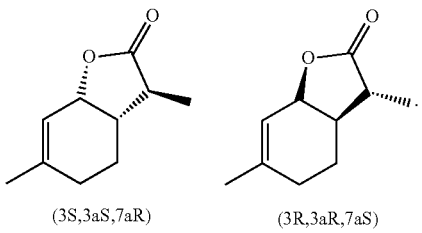

(3S,3aS,7aR)   (3R,3aR,7aS)

[15] The process according to [14] above, which further comprises the step of recrystallization to obtain the (3S,3aS, 7aR) isomer represented by the following formula:

[Formula 34]

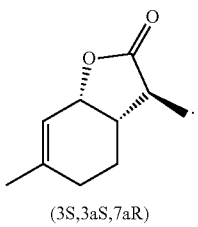

(3S,3aS,7aR)

[16] The process according to any one of [1] to [15] above, wherein all of the production steps are performed at a temperature of 0° C. or more to 130° C. or less, and none of the production steps requires any purification step by silica gel column chromatography.

Effect of the Invention

According to the present invention, wine lactone or a stereoisomer thereof or a mixture thereof can be produced in a simple manner through fewer steps without using any harmful or expensive reagents and without requiring reaction conditions of extremely low or high temperatures. Moreover, according to a preferred embodiment of the present invention, wine lactone can be produced in a highly selective manner. The process of the present invention is suitable for use on an industrial scale.

MODES FOR CARRYING OUT THE INVENTION

The production process of the present invention will be described in more detail below. The production process of the present invention is a process for producing a compound represented by formula (a), which is wine lactone or a stereoisomer thereof or a mixture thereof:

[Formula 35]

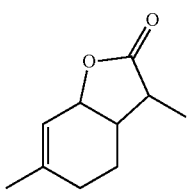

(a)

wherein said process is characterized by comprising steps A), B) and C) shown in the reaction scheme below:

[Formula 36]

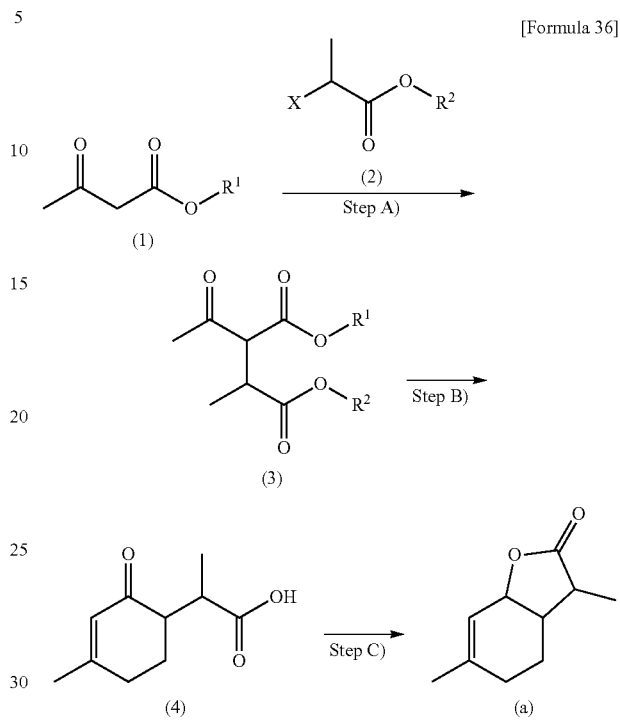

[wherein $R^1$ is an alkyl group containing 1 to 4 carbon atoms, $R^2$ is an alkyl group containing 1 to 4 carbon atoms, and X is a chlorine atom or a bromine atom].

Step B) is intended to obtain a compound represented by formula (4) through cyclization reaction of a compound represented by formula (3). Step B) includes cases such as where the compound represented by formula (3) is reacted under basic conditions and then hydrolyzed to obtain the compound represented by formula (4) (step B-1) and where the compound represented by formula (3) is reacted under basic conditions and decarboxylated in the presence of an inorganic salt (step B-2), followed by hydrolysis to obtain the compound represented by formula (4) (step B-3).

In another aspect, the production process of the present invention is a process for producing a compound represented by formula (a), which is wine lactone or a stereoisomer thereof or a mixture thereof:

[Formula 37]

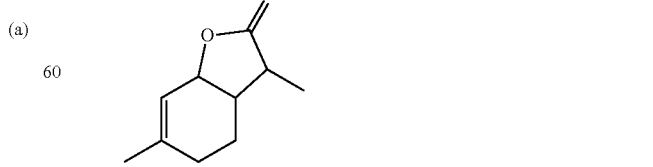

wherein said process is characterized by comprising steps A), B-2) and E) shown in the reaction scheme below:

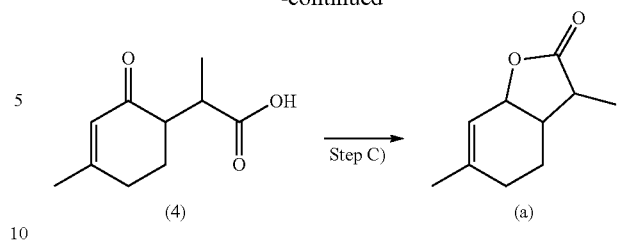

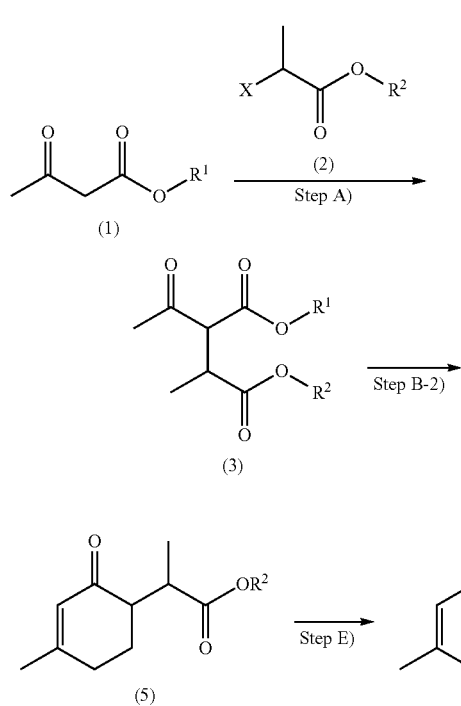

[wherein $R^1$ is an alkyl group containing 1 to 4 carbon atoms, $R^2$ is an alkyl group containing 1 to 4 carbon atoms, and X is a chlorine atom or a bromine atom].

Hereinafter, the process comprising step A), step B-1) and step C) is referred to as the first embodiment, the process comprising step A), step B-2), step B-3) and step C) is referred to as the second embodiment, and the process comprising step A), step B-2) and step E) is referred to as the third embodiment. Explanation will be made on each of these embodiments.

1. First Embodiment

The production process according to the first embodiment of the present invention is characterized by comprising step A), step B-1) and step C):

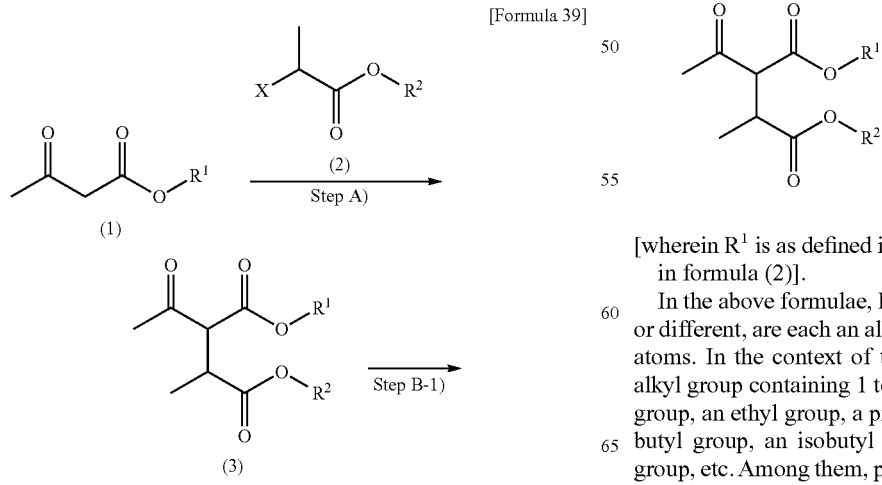

[wherein $R^1$ is an alkyl group containing 1 to 4 carbon atoms, $R^2$ is an alkyl group containing 1 to 4 carbon atoms, and X is a chlorine atom or a bromine atom].

Detailed explanation will be given below for each step.

(1) Step A)

Step A) is intended to react a β-keto ester represented by formula (1):

[Formula 40]

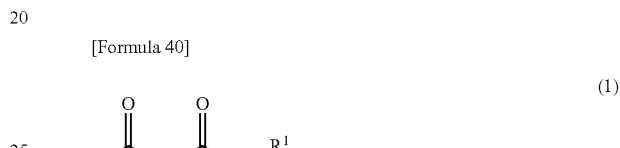

[wherein $R^1$ is an alkyl group containing 1 to 4 carbon atoms] with a 2-halo ester represented by formula (2):

[Formula 41]

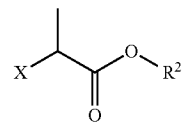

[wherein $R^2$ is an alkyl group containing 1 to 4 carbon atoms, and X is a chlorine atom or a bromine atom] under basic conditions to thereby obtain a 2-aceto-3-methyl-succinic acid ester represented by formula (3):

[Formula 42]

[wherein $R^1$ is as defined in formula (1), and $R^2$ is as defined in formula (2)].

In the above formulae, $R^1$ and $R^2$, which may be the same or different, are each an alkyl group containing 1 to 4 carbon atoms. In the context of this specification, examples of an alkyl group containing 1 to 4 carbon atoms include a methyl group, an ethyl group, a propyl group, an isopropyl group, a butyl group, an isobutyl group, a s-butyl group, a t-butyl group, etc. Among them, preferred are a methyl group and an ethyl group.

Examples of the 2-halo ester represented by formula (2) include the compounds shown below.

[Formula 43]

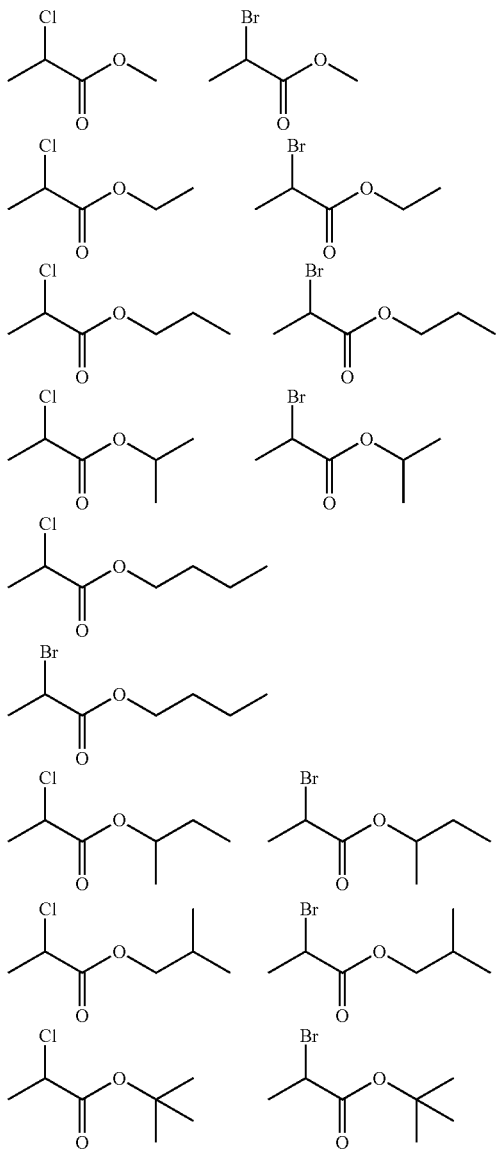

Among them, preferred are 2-bromopropionic acid alkyl esters and particularly preferred are methyl 2-bromopropionate and ethyl 2-bromopropionate.

The amount of the 2-halo ester represented by formula (2) to be used is selected as appropriate from the range of usually 0.5 to 10 molar equivalents, preferably 0.8 to 1.2 molar equivalents, relative to the β-keto ester represented by formula (1).

This step is performed under basic conditions. Examples of a base used for this purpose include inorganic bases and organic bases, etc.

Examples of inorganic bases include alkali metal or alkaline earth metal salts such as potassium carbonate, potassium hydroxide, lithium hydroxide, sodium bicarbonate, sodium carbonate, potassium bicarbonate, sodium hydroxide, magnesium carbonate, and calcium carbonate; as well as metal hydrides such as sodium hydride.

Examples of organic bases include alkali metal alkoxides such as potassium methoxide, sodium methoxide, lithium methoxide, sodium ethoxide, potassium isopropoxide, potassium tert-butoxide, and potassium naphthalenide; alkali metal or alkaline earth metal acetate salts such as sodium acetate, potassium acetate, magnesium acetate, and calcium acetate; organic amines such as triethylamine, diisopropylethylamine, N,N-dimethylaniline, piperidine, pyridine, 4-dimethylamino-pyridine, 1,5-diazabicyclo[4.3.0]non-5-ene, 1,8-diazabicyclo[5.4.0]undec-7-ene, tri-n-butylamine, and N-methylmorpholine; as well as quaternary ammonium salts, etc.

Among them, preferred are organic bases. In particular, sodium methoxide and sodium ethoxide are preferred for use.

The amount of a base to be used is selected as appropriate from the range of usually 0.5 to 10 molar equivalents, preferably 1.0 to 3.0 molar equivalents, relative to the β-keto ester represented by formula (1).

The reaction is preferably performed in the presence of a solvent. Examples of a solvent used for this purpose include aliphatic hydrocarbons such as pentane, hexane, heptane, octane, decane, and cyclohexane; aromatic hydrocarbons such as benzene, toluene, and xylene; halogenated hydrocarbons such as dichloromethane, 1,2-dichloroethane, chloroform, carbon tetrachloride, and o-dichlorobenzene; ethers such as diethyl ether, diisopropyl ether, tert-butyl methyl ether, dimethoxyethane, ethylene glycol diethyl ether, tetrahydrofuran, 1,4-dioxane, and 1,3-dioxolane; alcohols such as methanol, ethanol, 2-propanol, n-butanol, 2-ethoxyethanol, and benzyl alcohol; ketones such as acetone, methyl ethyl ketone, methyl isobutyl ketone, and cyclohexanone; esters such as methyl acetate, ethyl acetate, n-butyl acetate, and methyl propionate; amides such as formamide, N,N-dimethylformamide, and N,N-dimethylacetamide; sulfoxides such as dimethyl sulfoxide; cyano-containing organic compounds such as acetonitrile; as well as N-methylpyrrolidone, water, etc. These solvents may be used either alone or in combination as appropriate. Among them, alcohols are particularly preferred.

The amount of a solvent to be used is selected as appropriate from the range of usually 0.5- to 100-fold volume (ml) [solvent (ml)/substrate (g)] (the term "fold volume" is used hereinafter in the same meaning), preferably 1- to 40-fold volume, relative to the weight (g) of the β-keto ester represented by formula (1).

The reaction temperature of the above reaction is selected as appropriate from the range of usually 0° C. to 100° C., preferably 0° C. to 80° C. Likewise, the reaction time is selected as appropriate from the range of usually 0.5 to 20 hours, preferably 1 to 10 hours.

After completion of the reaction, the resulting 2-aceto-3-methyl-succinic acid ester represented by formula (3) may be used directly in the subsequent step without any secondary treatment or the like, or may be optionally subjected to secondary treatment, purification, isolation or the like before being used in the subsequent step. Techniques actually used for secondary treatment include known techniques such as solvent extraction, phasic transfer, salting-out, distillation, crystallization, recrystallization, etc. However, purification by silica gel column chromatography is not favorable in terms of cost-effectiveness or working efficiency, because it requires a large volume of solvent.

As to reaction conditions and other information on step A, reference may be made to the reaction described in Non-patent Document 5 (J. Org. Chem. 54, 1876-1883 (1989)), in which methyl 2-bromopropionate and methyl acetoacetate are reacted to obtain methyl 3-(methoxycarbonyl)-2-methyl-4-oxopentanoate.

(2) Step B-1)

Step B-1) is intended to react the 2-aceto-3-methyl-succinic acid ester represented by formula (3) obtained in step A) with methyl vinyl ketone under basic conditions, followed by hydrolysis to thereby obtain an α-methyl-γ-keto acid represented by formula (4):

[Formula 44]

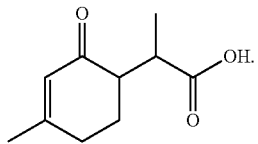

(4)

Methyl vinyl ketone used for this purpose may be a commercially available product. Alternatively, it is also possible to use a synthetic product. For example, methyl vinyl ketone may be obtained by being prepared through dehydration of 4-hydroxy-2-butanone, which can be easily synthesized by condensation between formalin and acetone, or by being prepared through Hofmann elimination of 4-amino-2-butanone (Mannich base), which is obtained by reaction of acetone, formaldehyde and an amine. Methyl vinyl ketone thus obtained may be purified by distillation or the like before use, or the crude reaction product may be used directly.

The amount of methyl vinyl ketone to be used is selected as appropriate from the range of usually 0.5 to 10 molar equivalents, preferably 0.8 to 1.5 molar equivalents, relative to the 2-aceto-3-methyl-succinic acid ester represented by formula (3).

This step is performed under basic conditions. Examples of a base used for this purpose include inorganic bases and organic bases, etc. Although it is possible to use the same inorganic and organic bases as listed in step A), inorganic bases are preferred for use in this step. Among them, preferred are potassium hydroxide and sodium hydroxide.

The amount of a base to be used is selected as appropriate from the range of usually 0.0001 to 10 molar equivalents, preferably 0.0005 to 3 molar equivalents, relative to the 2-aceto-3-methyl-succinic acid ester represented by formula (3).

The reaction is preferably performed in the presence of a solvent. Specific examples of a solvent include the same solvents as listed in step A). These solvents may be used either alone or in combination as appropriate. Among them, preferred are alcohols or sulfoxides.

The amount of a solvent to be used is selected as appropriate from the range of usually 0.5- to 100-fold volume, preferably 1- to 40-fold volume, relative to the 2-aceto-3-methyl-succinic acid ester represented by formula (3).

The reaction temperature of the above reaction is selected as appropriate from the range of usually 0° C. to 100° C., preferably 0° C. to 80° C. Likewise, the reaction time is selected as appropriate from the range of usually 0.5 to 20 hours, preferably 1 to 10 hours.

In step B-1), the reaction between the 2-aceto-3-methyl-succinic acid ester represented by formula (3) and methyl vinyl ketone is followed by hydrolysis reaction. The hydrolysis reaction is preferably performed by addition of an acid or a base.

Examples of an acid for use in the hydrolysis reaction include inorganic acids, organic acids and Lewis acids, etc.

Examples of inorganic acids include hydrochloric acid, hydrobromic acid, sulfuric acid, phosphoric acid, tetrafluoroboric acid, perchloric acid, periodic acid, etc.

Examples of organic acids include carboxylic acids such as formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, and glycolic acid; as well as sulfonic acids such as methanesulfonic acid, benzenesulfonic acid, p-toluenesulfonic acid, and trifluoromethanesulfonic acid.

Examples of Lewis acids include halogenated aluminum compounds such as aluminum chloride, and aluminum bromide; halogenated dialkylaluminum compounds such as diethylaluminum chloride, diethylaluminum bromide, and diisopropylaluminum chloride; trialkoxyaluminum compounds such as triethoxyaluminum, triisopropoxy-aluminum, and tri-tert-butoxyaluminum; halogenated titanium compounds such as titanium tetrachloride; tetraalkoxytitanium compounds such as tetraisopropoxytitanium; halogenated boron compounds such as boron trifluoride, boron trichloride, boron tribromide, and boron trifluoride diethyl ether complex; as well as halogenated zinc compounds such as zinc chloride, and zinc bromide.

Among them, preferred are inorganic acids, especially hydrochloric acid and sulfuric acid.

The amount of an acid to be used is selected as appropriate from the range of usually 0.001 to 10 molar equivalents, preferably 0.01 to 3 molar equivalents, relative to the 2-aceto-3-methyl-succinic acid ester represented by formula (3).

Examples of a base include inorganic bases and organic bases, etc. Specific examples of inorganic and organic bases include the same bases as listed in step A). Among them, preferred inorganic bases are potassium hydroxide and sodium hydroxide, while preferred organic bases are potassium methoxide, sodium methoxide, and sodium ethoxide.

The amount of a base to be used is selected as appropriate from the range of 0.001 to 10 molar equivalents, preferably 0.01 to 4 molar equivalents, relative to the 2-aceto-3-methyl-succinic acid ester represented by formula (3).

The hydrolysis reaction is preferably performed in a solvent.

Examples of a solvent include aliphatic hydrocarbons such as pentane, hexane, heptane, octane, decane, and cyclohexane; aromatic hydrocarbons such as benzene, toluene, and xylene; halogenated hydrocarbons such as dichloromethane, chloroform, carbon tetrachloride, and o-dichlorobenzene; ethers such as diethyl ether, diisopropyl ether, tert-butyl methyl ether, dimethoxyethane, ethylene glycol diethyl ether, tetrahydrofuran, 1,4-dioxane, and 1,3-dioxolane; alcohols such as methanol, ethanol, 2-propanol, n-butanol, 2-ethoxyethanol, and benzyl alcohol; polyhydric alcohols such as ethylene glycol, propylene glycol, 1,2-propanediol, and glycerine; acids such as formic acid, acetic acid, and propionic acid; sulfoxides such as dimethyl sulfoxide; as well as N-methylpyrrolidone, water, etc.

These solvents may be used either alone or in combination as appropriate. Among them, preferred are alcohols or sulfoxides.

The amount of a solvent to be used is selected as appropriate from the range of usually 0.5- to 100-fold volume, preferably 1- to 40-fold volume, relative to the 2-aceto-3-methyl-succinic acid ester represented by formula (3).

The reaction temperature of the hydrolysis reaction is selected as appropriate from the range of usually 0° C. to 100°

C., preferably 0° C. to 80° C. Likewise, the reaction time is selected as appropriate from the range of usually 0.5 to 24 hours, preferably 1 to 20 hours.

After completion of the reaction, the resulting α-methyl-γ-keto acid represented by formula (4) may be used directly in the subsequent step without any secondary treatment or the like, or may be optionally subjected to secondary treatment, purification, isolation or the like before being used in the subsequent step. Techniques actually used for secondary treatment are the same as those described in step A).

(3) Step C)

Step C) is intended to reduce the α-methyl-γ-keto acid represented by formula (4) obtained in step B-1):

[Formula 45]

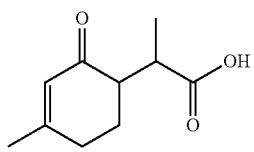

(4)

to thereby obtain a compound represented by formula (a), which is wine lactone or a stereoisomer thereof or a mixture thereof:

[Formula 46]

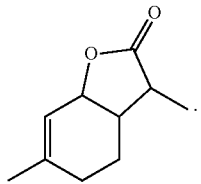

(a)

Although the reduction reaction in this step is not limited in any way, it is accomplished by reducing the ketone site of the α-methyl-γ-keto acid represented by formula (4) through hydride reduction, etc. Since a reducing reagent approaches the α-methyl-γ-keto acid represented by formula (4) through its spatially opened side, this step allows stereoselective production of (3S,3aS,7aR), (3R,3aR,7aS), (3R,3aS,7aR) and (3S,3aR,7aS) isomers represented by the following formulae:

[Formula 47]

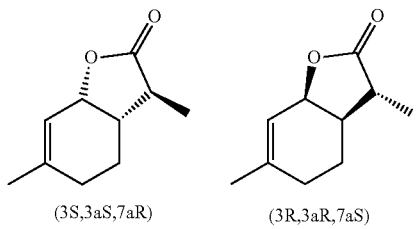

(3S,3aS,7aR)　　　(3R,3aR,7aS)

-continued

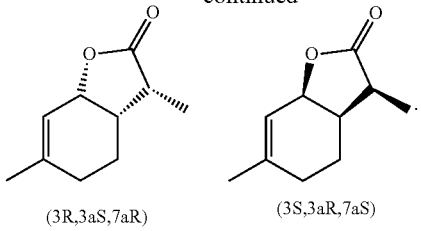

(3R,3aS,7aR)　　　(3S,3aR,7aS)

Examples of a reagent for hydride reduction include sodium borohydride, sodium cyanoborohydride, lithium triethylborohydride, lithium tri(sec-butyl)borohydride, potassium tri(sec-butyl)borohydride, lithium borohydride, zinc borohydride, lithium aluminum hydride, sodium bis(2-methoxyethoxy)aluminum hydride, diborane, diisobutylaluminum hydride, etc.

The amount of a reagent for hydride reduction to be used is selected as appropriate from the range of 0.01 to 10 molar equivalents, preferably 0.1 to 3 molar equivalents, relative to the α-methyl-γ-keto acid of (4).

The reduction reaction may optionally be performed in the presence of a reaction aid (e.g., cerium chloride, calcium chloride) to thereby selectively reduce the ketone on the ring of the α-methyl-γ-keto acid.

The reduction reaction is preferably performed in a solvent. Specific examples of a solvent include the same solvents as listed for the hydrolysis reaction in step B-1). These solvents may be used either alone or in combination as appropriate. Among them, preferred are alcohols.

The amount of a solvent to be used is selected as appropriate from the range of usually 0.5- to 100-fold volume, preferably 1- to 40-fold volume, relative to the α-methyl-γ-keto acid represented by formula (4).

The reaction temperature of the reduction reaction is selected as appropriate from the range of usually 0° C. to 100° C., preferably 0° C. to 80° C. Likewise, the reaction time is selected as appropriate from the range of usually 0.5 to 20 hours, preferably 1 to 10 hours.

Moreover, during the hydride reduction reaction, asymmetric hydrogenation reaction may optionally be caused under basic conditions and in the presence of a transition metal complex and a hydrogen gas to thereby obtain wine lactone of (3S,3aS,7aR) form in a highly selective manner.

Transition metal complexes used for this purpose may be those described in, e.g., JP 11-189600 A. Specific examples of transition metal complexes include, but are not particularly limited to, RuCl$_2$-[(R)-binap][(R,R)-dpen], RuCl$_2$-[(R)-binap][(R)-daipen], RuCl$_2$-[(R)-Tol-binap][(R,R)-dpen], RuCl$_2$-[(R)-Tol-binap] [(R)-daipen], RuCl$_2$-[(R)-DM-binap][(R,R)-dpen], RuCl$_2$-[(R)-DM-binap] [(R)-daipen], RuCl$_2$-[(S)-binap][(S,S)-dpen], RuCl$_2$-[(S)-binap][(S)-daipen], RuCl$_2$-[(S)-Tol-binap][(S,S)-dpen], RuCl$_2$-[(S)-Tol-binap][(S)-daipen], RuCl$_2$-[(S)-DM-binap][(S,S)-dpen], RuCl$_2$-[(S)-DM-binap][(S)-daipen], etc.

In the above complexes, binap represents 2,2'-bis-(diphenylphosphino)-1,1'-binaphthyl, Tol-binap represents 2,2'-bis-(di-p-tolylphosphino)-1,1'-binaphthyl, DM-binap represents 2,2'-bis[bis(3,5-dimethylphenyl)phosphino]-1,1'-binaphthyl, dpen represents 1,2-diphenyl-ethylenediamine, and daipen represents 1,1-di(4-methoxyphenyl)-2-isopropyl-1,2-ethylenediamine.

Although the amount of a transition metal complex to be used will vary depending on the type of reaction vessel, the mode of reaction or the degree of cost-effectiveness, it may be used at a molar ratio ranging from 1/10 to 1/100,000, preferably 1/50 to 1/10,000, relative to the reaction substrate, i.e., the α-methyl-γ-keto acid.

Examples of a base optionally used include alkali metal or alkaline earth metal salts such as potassium carbonate ($K_2CO_3$), potassium hydroxide (KOH), lithium hydroxide (LiOH), potassium methoxide ($KOCH_3$), potassium isopropoxide ($KOCH(CH_3)_2$), potassium tert-butoxide ($KOC(CH_3)_3$), lithium methoxide ($LiOCH_3$), potassium naphthalene ($KC_{10}H_8$), and lithium isopropoxide ($LiOCH(CH_3)_2$); as well as quaternary ammonium salts, etc. Among them, preferred are alkali metal or alkaline earth metal salts.

The amount of a base to be used is 0.001 to 10 molar equivalents, preferably 0.01 to 2 molar equivalents, relative to the α-methyl-γ-keto acid represented by formula (4).

Alternatively, the hydride reduction reaction may be replaced with asymmetric reduction reaction of the α-methyl-γ-keto acid represented by formula (4) in the presence of an optically active form of a ruthenium complex selected from compounds represented by formula (6) or (7) shown below and in the presence of a hydrogen donor to thereby obtain wine lactone of (3S,3aS,7aR) form in a highly selective manner.

Explanation will be given below for each of the ruthenium complexes represented by formulae (6) and (7).

The ruthenium complex represented by formula (6) is as follows:

[Formula 48]

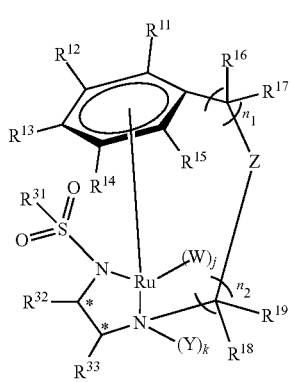

(6)

[wherein * represents an asymmetric carbon atom, $R^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—NR$^{20}$R$^{21}$), a 5- or 6-membered cyclic amino group, an acylamino group (—NH—CO—R$^{20}$), a hydroxyl group, an alkoxy group (—OR$^{20}$), an acyl group (—CO—R$^{20}$), a carboxyl group, an alkoxycarbonyl group (—COOR$^{20}$), a phenoxycarbonyl group, a mercapto group, an alkylthio group (—SR$^{20}$), a silyl group (—SiR$^{20}$R$^{21}$, R$^{22}$) and a nitro group (—NO$_2$), wherein R$^{20}$, R$^{21}$ and R$^{22}$ are each independently a hydrogen atom, an alkyl group containing 1 to 10 carbon atoms, or a cycloalkyl group containing 3 to 10 carbon atoms, Y is a hydrogen atom, W is a trifluoromethanesulfonyloxy group, a p-toluenesulfonyloxy group, a methanesulfonyloxy group, a benzenesulfonyloxy group, a hydrogen atom, or a halogen atom, j and k are each independently 0 or 1, provided that j+k is not 1, $R^{32}$ and $R^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, $R^{32}$ and $R^{33}$ may together form a ring, $R^{11}$, $R^{12}$, $R^{13}$, $R^{14}$ and $R^{15}$ are each independently a hydrogen atom, an alkyl group containing 1 to 10 carbon atoms, or an alkoxy group containing 1 to 10 carbon atoms, $R^{16}$, $R^{17}$, $R^{18}$ and $R^{19}$ are each independently a hydrogen atom, a hydroxyl group, an alkyl group containing 1 to 10 carbon atoms, or an alkoxy group containing 1 to 10 carbon atoms, or alternatively, $R^{16}$ and $R^{17}$ may form a carbonyl group together with their adjacent carbon atom and/or $R^{18}$ and $R^{19}$ may form a carbonyl group together with their adjacent carbon atom, Z is an oxygen atom or a sulfur atom, $n_1$ is 1 or 2, and $n_2$ is an integer of 1 to 3].

The ruthenium complex represented by formula (7) is as follows:

[Formula 49]

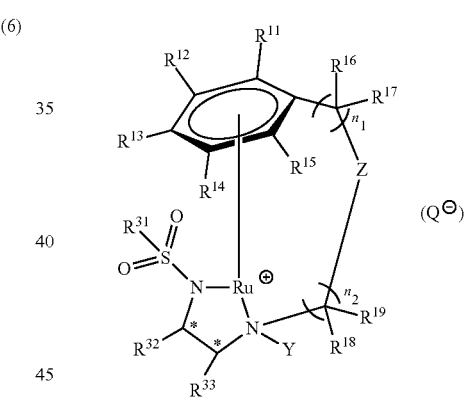

(7)

[wherein * represents an asymmetric carbon atom, $R^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—NR$^{20}$R$^{21}$), a 5- or 6-membered cyclic amino group, an acylamino group (—NH—CO—R$^{20}$), a hydroxyl group, an alkoxy group (—OR$^{20}$), an acyl group (—CO—R$^{20}$), a carboxyl group, an alkoxycarbonyl group (—COOR$^{20}$), a phenoxycarbonyl group, a mercapto group, an alkylthio group (—SR$^{20}$), a silyl group (—SiR$^{20}$R$^{21}$R$^{22}$) and a nitro group (—NO$_2$), wherein R$^{20}$, R$^{21}$ and R$^{22}$ are each independently a hydrogen atom, an alkyl group containing 1 to 10 carbon atoms, or a cycloalkyl group containing 3 to 10 carbon atoms, Y is a hydrogen atom, $R^{32}$ and $R^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, $R^{32}$ and $R^{33}$ may together form a ring, $R^{11}$, $R^{12}$, $R^{13}$, $R^{14}$ and $R^{15}$ are each independently a hydrogen atom, an alkyl group containing 1 to 10 carbon atoms, or an alkoxy group containing 1 to 10 carbon atoms, $R^{16}$, $R^{17}$, $R^{18}$ and $R^{19}$ are each independently a hydrogen atom, a hydroxyl group, an alkyl group containing 1 to 10 carbon atoms, or an alkoxy group containing 1 to 10 carbon atoms, or alternatively, $R^{16}$ and $R^{17}$ may form a carbonyl group together with their adjacent carbon atom and/or $R^{18}$ and $R^{19}$ may form a carbonyl group together with their adjacent carbon atom, Z is an oxygen atom or a sulfur atom, $Q^-$ is a counter anion, $n_1$ is 1 or 2, and $n_2$ is an integer of 1 to 3].

In formulae (6) and (7), examples of the alkyl group containing 1 to 10 carbon atoms represented by $R^{31}$ include linear or branched alkyl groups containing 1 to 10 carbon atoms, preferably 1 to 5 carbon atoms. Specific examples of such alkyl groups include a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group and a n-decyl group, etc.

In formulae (6) and (7), the halogenated alkyl group containing 1 to 10 carbon atoms represented by $R^{31}$ is an alkyl group containing 1 to 10 carbon atoms derived from the above linear or branched alkyl groups (e.g., a methyl group, an ethyl group, a n-propyl group, an isopropyl group, a n-butyl group, a n-hexyl group) by being substituted with one or more halogen atoms such as a fluorine atom, a chlorine atom, a bromine atom, etc. Specific examples include perfluoroalkyl groups such as a trifluoromethyl group, a pentafluoroethyl group, a heptafluoropropyl group, etc.

In formulae (6) and (7), examples of an aryl group in the aryl group represented by $R^{31}$ which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—$NR^{20}R^{21}$), a 5- or 6-membered cyclic amino group, an acylamino group (—NH—CO—$R^{20}$), a hydroxyl group, an alkoxy group (—$OR^{20}$), an acyl group (—CO—$R^{20}$), a carboxyl group, an alkoxycarbonyl group (—$COOR^{20}$), a phenoxycarbonyl group, a mercapto group, an alkylthio group (—$SR^{20}$), a silyl group (—$SiR^{20}R^{21}R^{22}$) and a nitro group (—$NO_2$) include monocyclic, polycyclic or condensed cyclic aryl groups containing 1 to 20 carbon atoms, preferably 6 to 12 carbon atoms, as exemplified by a phenyl group or a naphthyl group, etc.

Examples of an alkyl group containing 1 to 10 carbon atoms as a substituent on the above aryl group include alkyl groups as listed above.

Examples of a halogenated alkyl group containing 1 to 10 carbon atoms include halogenated alkyl groups as listed above, such as perfluoroalkyl groups.

Examples of a halogen atom include a fluorine atom or a chlorine atom, etc.

Examples of an alkylamino group represented by —$NR^{20}R^{21}$ include monoalkylamino groups such as an N-methylamino group, an N,N-dimethylamino group, an N,N-diisopropylamino group or an N-cyclohexylamino group, as well as dialkylamino groups.

Examples of a 5- or 6-membered cyclic amino group include 5- to 6-membered unsaturated or saturated heterocyclic groups having one or two nitrogen atoms, as exemplified by a pyrrolidinyl group, a piperidino group, a morphonyl group, etc.

Examples of an acyl group represented by —CO—$R^{20}$ include a formyl group, an acetyl group, a propionyl group, a butyryl group, a pivaloyl group, a pentanoyl group, or a hexanoyl group, etc.

Examples of an acylamino group represented by —NH—CO—$R^{20}$ include a formylamino group, an acetylamino group, a propionylamino group, a pivaloylamino group, a pentanoylamino group, or a hexanoylamino group, etc.

Examples of an alkoxy group represented by —$OR^{20}$ include a methoxy group, an ethoxy group, a n-propoxy group, an isopropoxy group, a n-butoxy group, a s-butoxy group, an isobutoxy group, a t-butoxy group, a n-pentyloxy group, a 2-methylbutoxy group, a 3-methylbutoxy group, a 2,2-dimethylpropyloxy group, a n-hexyloxy group, a 2-methylpentyloxy group, a 3-methylpentyloxy group, a 4-methylpentyloxy group, a 5-methylpentyloxy group or a cyclohexyloxy group, etc.

Examples of an alkoxycarbonyl group represented by —$COOR^{20}$ include a methoxycarbonyl group, an ethoxycarbonyl group, a n-propoxycarbonyl group, an isopropoxycarbonyl group, a n-butoxycarbonyl group, a t-butoxycarbonyl group, a pentyloxycarbonyl group, a hexyloxycarbonyl group or a 2-ethylhexyloxycarbonyl group, etc.

Examples of an alkylthio group represented by —$SR^{20}$ include a methylthio group, an ethylthio group, a n-propylthio group, an isopropylthio group, a n-butylthio group, a s-butylthio group, an isobutylthio group, a t-butylthio group, a pentylthio group, a hexylthio group or a cyclohexyl group, etc.

Examples of a silyl group represented by —$SiR^{20}R^{21}R^{22}$ include a trimethylsilyl group, a triisopropylsilyl group, a t-butyldimethylsilyl group, a t-butyldiphenylsilyl group or a triphenylsilyl group, etc.

In the above formulae, $R^{20}$, $R^{21}$ and $R^{22}$ are each independently a hydrogen atom, an alkyl group containing 1 to 10 carbon atoms, or a cycloalkyl group having 3 to 10 carbon atoms.

Examples of the alkyl group containing 1 to 10 carbon atoms intended as $R^{20}$, $R^{21}$ or $R^{22}$ include alkyl groups as listed above.

Examples of the cycloalkyl group having 3 to 10 carbon atoms intended as $R^{20}$, $R^{21}$ or $R^{22}$ include monocyclic, polycyclic or condensed cyclic saturated or unsaturated 3- to 7-membered cycloalkyl groups having 3 to 10 carbon atoms.

Examples of an aryl group which may be substituted with these substituents include a phenyl group, an o-, m- or p-tolyl group, an o-, m- or p-ethylphenyl group, an o-, m- or p-isopropylphenyl group, an o-, m- or p-t-butylphenyl group, a 2,4,6-trimethylphenyl group, a 3,5-xylyl group, a 2,4,6-triisopropylphenyl group, an o-, m- or p-trifluoromethylphenyl group, an o-, m- or p-fluorophenyl group, an o-, m- or p-chlorophenyl group, as well as a pentafluorophenyl group, etc.

In formulae (6) and (7), examples of the alkyl group containing 1 to 10 carbon atoms represented by $R^{32}$ or $R^{33}$ include linear or branched alkyl groups containing 1 to 10 carbon atoms, preferably 1 to 5 carbon atoms. Specific examples of such alkyl groups include a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group and a n-decyl group, etc.

In formulae (6) and (7), examples of an alkyl group containing 1 to 10 carbon atoms in the phenyl group represented by $R^{32}$ or $R^{33}$ which may be substituted with at least one substituent selected from the group consisting of an alkyl group containing 1 to 10 carbon atoms, an alkoxy group containing 1 to 10 carbon atoms and a halogen atom include alkyl groups as listed above.

Examples of an alkoxy group containing 1 to 10 carbon atoms include linear or branched alkoxy groups containing 1 to 10 carbon atoms, preferably 1 to 5 carbon atoms. Specific examples of such alkoxy groups include a methoxy group, an ethoxy group, a n-propoxy group, an isopropoxy group, a n-butoxy group, an isobutoxy group, a s-butoxy group, a t-butoxy group, a n-pentyloxy group, a n-hexyloxy group, a n-heptyloxy group, a n-octyloxy group, a n-nonyloxy group and a n-decyloxy group, etc.

Examples of a halogen atom include a fluorine atom, a chlorine atom and a bromine atom.

In formulae (6) and (7), examples of the cycloalkyl group containing 3 to 8 carbon atoms represented by $R^{32}$ or $R^{33}$ include monocyclic, polycyclic or bridged cycloalkyl groups containing 3 to 8 carbon atoms, preferably 5 to 8 carbon atoms. Specific examples include a cyclopropyl group, a cyclobutyl group, a cyclopentyl group, a cyclohexyl group, a cycloheptyl group and a cyclooctyl group, etc. These cycloalkyl groups may be substituted with an alkyl group such as a methyl group, an isopropyl group, a t-butyl group, etc.

When $R^{32}$ and $R^{33}$ together form a ring, $R^{32}$ and $R^{33}$ are taken together to form a linear or branched alkylene group containing 2 to 10 carbon atoms, preferably 3 to 10 carbon atoms, and further form a 4- to 8-membered, preferably 5- to 8-membered cycloalkane ring, together with their adjacent asymmetric carbon atoms.

Preferred cycloalkane rings include a cyclopentane ring, a cyclohexane ring and a cycloheptane ring. These rings may have a substituent such as an alkyl group, as exemplified by a methyl group, an isopropyl group, a t-butyl group, etc.

In the arene moiety shown in formula (6) or (7), $R^{11}$, $R^{12}$, $R^{13}$, $R^{14}$ and $R^{15}$ are each independently a hydrogen atom, an alkyl group containing 1 to 10 carbon atoms, or an alkoxy group containing 1 to 10 carbon atoms.

Examples of an alkyl group containing 1 to 10 carbon atoms include alkyl groups as listed above. Specific examples include a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group and a n-decyl group, etc.

Examples of an alkoxy group containing 1 to 10 carbon atoms include linear or branched alkoxy groups as listed above. Specific examples of such alkoxy groups include a methoxy group, an ethoxy group, a n-propoxy group, an isopropoxy group, a n-butoxy group, an isobutoxy group, a s-butoxy group, a t-butoxy group, a n-pentyloxy group, a n-hexyloxy group, a n-heptyloxy group, a n-octyloxy group, a n-nonyloxy group and a n-decyloxy group, etc.

In formulae (6) and (7), $R^{16}$, $R^{17}$, $R^{18}$ and $R^{19}$, which are defined as substituents on the carbon atoms of the chain moiety connecting the arene site and the diamine moiety, each independently represent a hydrogen atom, a hydroxyl group, an alkyl group containing 1 to 10 carbon atoms, or an alkoxy group containing 1 to 10 carbon atoms.

Examples of an alkyl group containing 1 to 10 carbon atoms include alkyl groups as listed above. Specific examples include a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group and a n-decyl group, etc.

Examples of an alkoxy group containing 1 to 10 carbon atoms include linear or branched alkoxy groups as listed above. Specific examples of such alkoxy groups include a methoxy group, an ethoxy group, a n-propoxy group, an isopropoxy group, a n-butoxy group, an isobutoxy group, a s-butoxy group, a t-butoxy group, a n-pentyloxy group, a n-hexyloxy group, a n-heptyloxy group, a n-octyloxy group, a n-nonyloxy group and a n-decyloxy group, etc.

Preferred examples of the —($-C(R^{16})R^{17}-)_{n_1}$- group include, but are not limited to, a —$CH_2$— group, a —CH($CH_3$)— group and a —CO— group, etc.

Preferred examples of the —($-C(R^{18})R^{19}-)_{n_2}$- group include, but are not limited to, a —$CH_2$—$CH_2$— group, etc.

In formulae (6) and (7), Z is an oxygen atom (—O—) or a sulfur atom (—S—).

In formula (6), k and j are each an integer of 0 or 1, provided that j+k is not 1. Namely, if k is 1, j is also 1, and if k is 0, j is also 0. When k is 1, Y is a hydrogen atom.

When j is 1 in formula (6), W may be any of a trifluoromethanesulfonyloxy group, a p-toluenesulfonyloxy group, a methanesulfonyloxy group, a benzenesulfonyloxy group, a hydrogen atom or a halogen atom. Preferred as W is a halogen atom, more specifically a chlorine atom, by way of example.

The hydrogen atoms intended as Y in formulae (6) and (7) and as W in formula (6) may be not only normal hydrogen atoms, but also isotopes thereof. Preferred isotopes include deuterium atoms.

$Q^-$ in formula (7) represents a counter anion. Specific examples of a counter anion include alkyl- or arenesulfonyloxy ions such as a trifluoromethanesulfonyloxy ion ($TfO^-$), a p-toluenesulfonyloxy ion ($TsO^-$), a methanesulfonyloxy ion ($MsO^-$), and a benzenesulfonyloxy ion ($BsO^-$); as well as ions such as $BF_4^-$, $SbF_6^-$, $CF_3COO^-$, $CH_3COO^-$, $PF_6^-$, $NO_3^-$, $ClO_4^-$, $SCN^-$, $OCN^-$, $ReO_4^-$, $MoO_4^-$, $BPh_4^-$, $B(C_6F_5)_4^-$, and $B(3,5-(CF_3)_2C_6F_3)_4^-$.

Among candidate compounds for the ruthenium complex represented by formula (6), preferred are those in which $R^{31}$ is an alkyl group containing 1 to 10 carbon atoms; or an aryl group which may be substituted with at least one substituent selected from the group consisting of an alkyl group containing 1 to 10 carbon atoms and a halogenated alkyl group containing 1 to 10 carbon atoms, Y is a hydrogen atom, W is a halogen atom, $R^{32}$ and $R^{33}$ are each independently an alkyl group containing 1 to 10 carbon atoms; or a phenyl group which may be substituted with at least one substituent selected from the group consisting of an alkyl group containing 1 to 10 carbon atoms, an alkoxy group containing 1 to 10 carbon atoms and a halogen atom, $R^{11}$, $R^{12}$, $R^{13}$, $R^{14}$ and $R^{15}$ are each independently a hydrogen atom or an alkyl group containing 1 to 10 carbon atoms, $R^{16}$, $R^{17}$, $R^{18}$ and $R^{19}$ are each independently a hydrogen atom, Z is an oxygen atom or a sulfur atom, j=1, and k=1, $n_1$ is 1, and $n_2$ is 2.

Likewise, among candidate compounds represented by formula (7), preferred are those in which $R^{31}$ is an alkyl group containing 1 to 10 carbon atoms; or an aryl group which may be substituted with at least one substituent selected from the group consisting of an alkyl group containing 1 to 10 carbon atoms and a halogenated alkyl group containing 1 to 10 carbon atoms, Y is a hydrogen atom, $R^{32}$ and $R^{33}$ are each independently an alkyl group containing 1 to 10 carbon atoms; or a phenyl group which may be substituted with at least one substituent selected from the group consisting of an alkyl group containing 1 to 10 carbon atoms, an alkoxy group containing 1 to 10 carbon atoms and a halogen atom, $R^{11}$, $R^{12}$, $R^{13}$, $R^{14}$ and $R^{15}$ are each independently a hydrogen atom or an alkyl group containing 1 to 10 carbon atoms, $R^{16}$, $R^{17}$, $R^{18}$ and $R^{19}$ are each independently a hydrogen atom, Z is an oxygen atom or a sulfur atom, $Q^-$ is a counter anion, $n_1$ is 1, and $n_2$ is 2.

Among them, preferred is the ruthenium complex represented by formula (6). Among candidates for the ruthenium complex represented by formula (6), more preferred is the compound shown below.

[Formula 50]

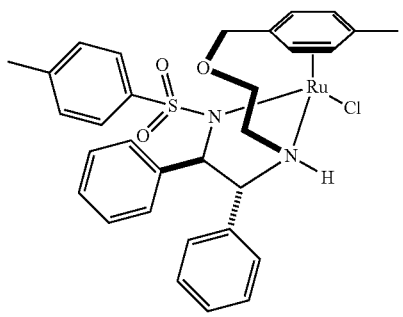

These candidates for the ruthenium complex represented by formula (6) can be produced according to the procedures described in J. Am. Chem. Soc., 2011, 133, 14960-14963, JP 2012-67071 A and WO2012/26201 A1. Candidates for the ruthenium complex represented by formula (7) can be produced according to the procedures described in JP 2012-67071 A and WO2012/26201 A1. Alternatively, commercially available products may be used. Examples include (R,R)-Ts-DENEB™, which is commercially available from STREM Inc., for the ruthenium complex represented by formula (6).

This asymmetric reduction reaction is accomplished by reacting the α-methyl-γ-keto acid represented by formula (4) with an optically active form of a ruthenium complex selected from the compounds represented by formula (6) or (7) in the presence of a hydrogen donor.

Any hydrogen donor may be used as long as it is commonly used for hydrogen-transfer reduction reaction, as exemplified by formic acid or an alkali metal salt thereof, isopropanol which is an alcohol having a hydrogen atom at the α-position of the carbon atom, on which a hydroxyl group is substituted, etc.

This asymmetric reduction reaction is preferably performed in the presence of a base. Examples of a base include tertiary organic amines such as trimethylamine, triethylamine, triisopropylamine, 1,4-diazabicyclo[2,2,2]octane (DABCO) and 1,8-diazabicyclo[5,4,0]undec-7-ene (DBU); as well as inorganic bases such as LiOH, NaOH, KOH, and $K_2CO_3$. Preferred bases are triethylamine and DABCO.

Such a base is used in an excess amount, e.g., in 1- to 100000-fold molar excess, relative to the ruthenium complex represented by formula (6) or (7). In the case of using triethylamine, it is preferably used in 1- to 10000-fold molar excess, relative to the ruthenium complex.

Among combinations between hydrogen donor and base, when the hydrogen donor is formic acid, an amine is preferred for use as a base. In this case, formic acid and the amine may be added separately to the reaction system, or an azeotropic mixture may be prepared from formic acid and the amine before use. Preferred examples of an azeotropic mixture between formic acid and amine include those of formic acid:amine=1:1 to 5:2 (molar ratio), etc.

Although the reaction may usually be accomplished by using the hydrogen donor as a reaction solvent if it is in a liquid state, toluene, tetrahydrofuran, acetonitrile, dimethylformamide, dimethyl sulfoxide, acetone, methylene chloride, methanol and other non-hydrogen-donating solvents may be used either alone or in combination as a cosolvent to dissolve the α-methyl-γ-keto acid. For example, in the case of using an alkali metal salt of formic acid, the reaction may be performed in a two-phase system where water is used as a cosolvent in combination with an organic solvent to dissolve the alkali metal salt of formic acid. In this case, a phase-transfer catalyst may also be used to accelerate the reaction.

The amount of the ruthenium complex to be used as a catalyst is selected such that the molar ratio (S/C) of the substrate, i.e., the α-methyl-γ-keto acid (S) relative to ruthenium metal atoms (C) is in the range of 10 to 1000000, preferably 100 to 15000.

As to the amount of the hydrogen donor relative to the α-methyl-γ-keto acid, it is usually used in an equimolar amount or more. When the hydrogen donor is formic acid or an alkali metal salt thereof, it is preferably used in 1.0-fold molar excess or more and used in the range of 20-fold molar excess or less, preferably 10-fold molar excess or less. On the other hand, when the hydrogen donor is isopropanol, etc, it is used in a large excess amount (10-fold molar excess or more) relative to the α-methyl-γ-keto acid in terms of reaction equilibrium, and usually used in the range of 1000-fold molar excess or less.

The reaction temperature is selected from the range of 0° C. to 100° C., preferably 0° C. to 70° C.

The reaction pressure is not limited in any way, and it is usually 0.05 to 0.2 MPa, preferably under normal pressure.

The reaction time will vary depending on the catalyst ratio, but it is 1 to 100 hours, usually 2 to 90 hours.

In view of the foregoing, in the first embodiment, it is possible to obtain the compound represented by formula (a):

[Formula 51]

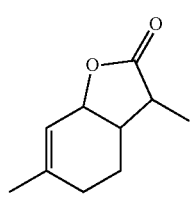

(a)

through step A), step B-1) and step C). As described above, in this embodiment, modifications to the reduction reaction in step C) allow highly selective production of wine lactone under normal reaction conditions without using any harmful or expensive reagents.

2. Second Embodiment

The production process according to the second embodiment of the present invention comprises step A), step B-2), step B-3) and step C):

[Formula 52]

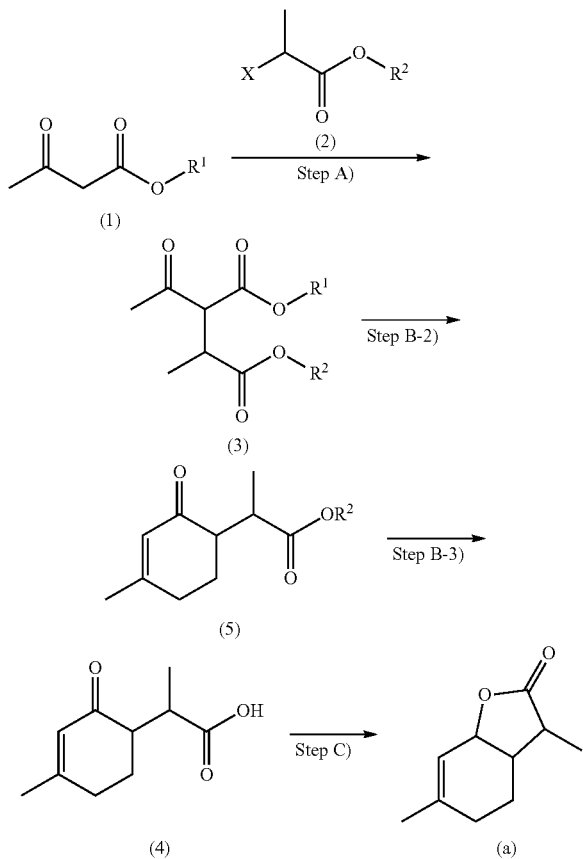

[wherein $R^1$ is an alkyl group containing 1 to 4 carbon atoms, $R^2$ is an alkyl group containing 1 to 4 carbon atoms, and X is a chlorine atom or a bromine atom].

Among the above steps in the second embodiment, step A) and step C) are the same as those of the first embodiment and their explanation will be omitted. Detailed explanation will be given below for step B-2) and step B-3).

(1) Step B-2)

Step B-2) is intended to react the 2-aceto-3-methyl-succinic acid ester obtained in step A) with methyl vinyl ketone under basic conditions, followed by decarboxylation reaction to thereby obtain an α-methyl-γ-keto acid ester represented by formula (5):

[Formula 53]

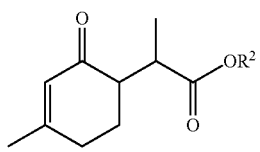

[wherein $R^2$ is as defined in formula (2)].

Methyl vinyl ketone used in this reaction may be either a commercially available product or a synthetic product, as described above in the first embodiment.

The amount of methyl vinyl ketone to be used is selected as appropriate from the range of usually 0.5 to 10 molar equivalents, preferably 0.8 to 1.5 molar equivalents, relative to the 2-aceto-3-methyl-succinic acid ester represented by formula (3).

In step B-2), the reaction is performed under basic conditions. Examples of a base used for this purpose include inorganic bases and organic bases, etc. It is possible to use the same inorganic and organic bases as those used in step B-1).

The amount of a base to be used is selected as appropriate from the range of usually 0.0001 to 10 molar equivalents, preferably 0.0005 to 3 molar equivalents, relative to the 2-aceto-3-methyl-succinic acid ester represented by formula (3).

The reaction is preferably performed in the presence of a solvent. Specific examples of a solvent include the same solvents as listed for the reaction between the 2-aceto-3-methyl-succinic acid ester represented by formula (3) and methyl vinyl ketone in step B-1). These solvents may be used either alone or in combination as appropriate. Among them, preferred are alcohols or sulfoxides.

The amount of a solvent to be used is selected as appropriate from the range of usually 0.5- to 100-fold volume, preferably 1- to 40-fold volume, relative to the 2-aceto-3-methyl-succinic acid ester represented by formula (3).

The reaction temperature of the above reaction is selected as appropriate from the range of usually 0° C. to 100° C., preferably 0° C. to 80° C. Likewise, the reaction time is selected as appropriate from the range of usually 0.5 to 20 hours, preferably 1 to 10 hours.

In step B-2), the reaction between the 2-aceto-3-methyl-succinic acid ester represented by formula (3) and methyl vinyl ketone under basic conditions is followed by decarboxylation reaction. The decarboxylation reaction is preferably performed by addition of an inorganic salt. It should be noted that the decarboxylation reaction may be performed without removing the solvent or may be performed after removing the solvent. Alternatively, the solvent may be removed and replaced with a fresh one before the reaction is performed.

Examples of an inorganic salt for use in the decarboxylation reaction include sodium chloride, magnesium chloride, potassium chloride, calcium chloride, sodium cyanide, magnesium cyanide, potassium cyanide, calcium cyanide, etc. Among them, preferred are sodium chloride and magnesium chloride.

The amount of an inorganic salt to be used is selected as appropriate from the range of usually 0.01 to 10 molar equivalents, preferably 0.1 to 5 molar equivalents, relative to the 2-aceto-3-methyl-succinic acid ester represented by formula (3).

Specific examples of a solvent for use in the decarboxylation reaction include the same solvents as listed for the reaction between the 2-aceto-3-methyl-succinic acid ester represented by formula (3) and methyl vinyl ketone in step B-1). These solvents may be used either alone or in combination as appropriate. Among them, preferred are sulfoxides.

The amount of a solvent to be used in the decarboxylation reaction is selected as appropriate from the range of usually 0.5- to 100-fold volume, preferably 1- to 40-fold volume, relative to the 2-aceto-3-methyl-succinic acid ester represented by formula (3).

The reaction temperature of the decarboxylation reaction is selected as appropriate from the range of usually 50° C. to 130° C., preferably 80° C. to 130° C. The reaction time is selected as appropriate from the range of usually 0.5 to 30 hours, preferably 1 to 20 hours.

After completion of the above reaction, the resulting α-methyl-γ-keto acid ester represented by formula (5) may be used directly in the subsequent step without any secondary treatment or the like, or may be optionally subjected to secondary treatment, purification, isolation or the like before being used in the subsequent step. Techniques actually used for secondary treatment are the same as those described above.

(2) Step B-3)

Step B-3) is intended to hydrolyze the α-methyl-γ-keto acid ester represented by formula (5) obtained in step B-2) to thereby obtain an α-methyl-γ-keto acid represented by formula (4):

[Formula 54]

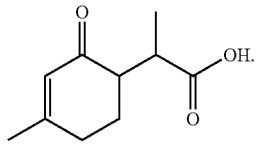

(4)

The hydrolysis of the α-methyl-γ-keto acid ester represented by formula (5) is preferably performed in the presence of an acid or a base. Specific examples of an acid or a base, which can be used for this purpose, include those which are listed as compounds available for use in hydrolysis in step B-1).

The amount of an acid to be used is selected as appropriate from the range of usually 0.001 to 10 molar equivalents, preferably 0.01 to 3 molar equivalents, relative to the α-methyl-γ-keto acid ester represented by formula (5).

The amount of a base to be used is selected as appropriate from the range of 0.001 to 10 molar equivalents, preferably 0.01 to 3 molar equivalents, relative to the α-methyl-γ-keto acid ester represented by formula (5).

In this step, the hydrolysis may be performed in the presence or absence of a solvent.

When the hydrolysis is performed in the presence of a solvent, examples of a solvent, which can be used for this purpose, include the same solvents as those which are listed as solvents available for use in hydrolysis in step B-1). Among them, preferred are alcohols, sulfoxides, and water.

The amount of a solvent to be used is selected as appropriate from the range of usually 0.5- to 100-fold volume, preferably 1- to 40-fold volume, relative to the α-methyl-γ-keto acid ester represented by formula (5).

The reaction temperature is selected as appropriate from the range of usually 0° C. to 100° C., preferably 0° C. to 80° C. Likewise, the reaction time is selected as appropriate from the range of usually 0.5 to 24 hours, preferably 1 to 20 hours.

After completion of the reaction, the resulting α-methyl-γ-keto acid represented by formula (4) may be used directly in the subsequent step without any secondary treatment or the like, or may be optionally subjected to secondary treatment, purification, isolation or the like before being used in the subsequent step. Techniques actually used for secondary treatment are the same as those described above.

Also in the second embodiment, modifications to the reduction reaction in step C) following step B-3) allow highly selective production of wine lactone under normal reaction conditions without using any harmful or expensive reagents.

3. Third Embodiment

The production process according to the third embodiment of the present invention comprises step A), step B-2) and step E):

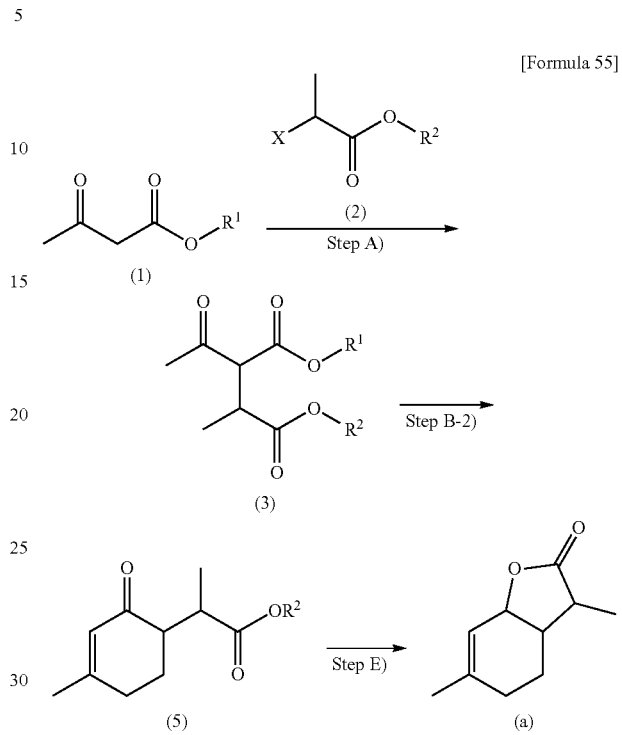

[Formula 55]

[wherein $R^1$ is an alkyl group containing 1 to 4 carbon atoms, $R^2$ is an alkyl group containing 1 to 4 carbon atoms, and X is a chlorine atom or a bromine atom].

Among the above steps in the third embodiment, step A) is the same as that of the first embodiment, while step B-2) is the same as that of the second embodiment. Thus, their explanation will be omitted. Detailed explanation will be given below for step E).

(1) Step E)

In a first case, step E) is intended for reduction reaction of the α-methyl-γ-keto acid ester obtained in step B-2) in the presence of a ruthenium complex selected from compounds represented by formula (6) or (7) and in the presence of a hydrogen donor to thereby obtain a compound represented by formula (a):

[Formula 56]

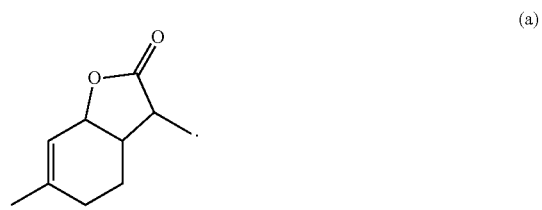

(a)

The ruthenium complexes represented by formulae (6) and (7) may be the same as those explained in step C) of the above first embodiment. Preferred compounds are also the same as explained in step C) of the above first embodiment, and their explanation will be omitted. However, in step E), the asterisk (*) in formulae (6) and (7) is intended to mean that the carbon atom indicated with * may be an asymmetric carbon atom.

When this carbon atom is an asymmetric carbon atom, formulae (6) and (7) may each represent an optically active form, a mixture of optically active forms, or a racemate (including racemic compounds). Among them, formulae (6) and (7) each preferably represent an optically active form.

Among them, preferred is the ruthenium complex represented by formula (6). Among candidates for the ruthenium complex represented by formula (6), more preferred is the compound shown below.

[Formula 57]

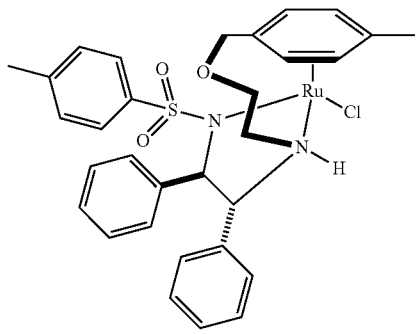

Step E) is accomplished by reacting the α-methyl-γ-keto acid ester represented by formula (5) with a ruthenium complex selected from formulae (6) and (7) in the presence of a hydrogen donor.

Any hydrogen donor may be used as long as it is commonly used for hydrogen-transfer reduction reaction, as exemplified by formic acid or an alkali metal salt thereof, isopropanol which is an alcohol having a hydrogen atom at the α-position of the carbon atom, on which a hydroxyl group is substituted, etc.

Step E) is preferably performed in the presence of a base. Examples of a base include tertiary organic amines such as trimethylamine, triethylamine, triisopropylamine, 1,4-diazabicyclo[2,2,2]octane (DABCO), and 1,8-diazabicyclo[5,4,0]undec-7-ene (DBU), as well as inorganic bases such as LiOH, NaOH, KOH, $K_2CO_3$. Preferred bases are triethylamine and DABCO.

Such a base is used in an excess amount, e.g., in 1- to 100000-fold molar excess, relative to the ruthenium complex represented by formula (6) or (7). In the case of using triethylamine, it is preferably used in 1- to 10000-fold molar excess, relative to the ruthenium complex.

Among combinations between hydrogen donor and base, when the hydrogen donor is formic acid, an amine is preferred for use as a base. In this case, formic acid and the amine may be added separately to the reaction system, or an azeotropic mixture may be prepared from formic acid and the amine before use. Preferred examples of an azeotropic mixture between formic acid and amine include those of formic acid:amine=1:1 to 5:2 (molar ratio), etc.

Although the reaction may usually be accomplished by using the hydrogen donor as a reaction solvent if it is in a liquid state, toluene, tetrahydrofuran, acetonitrile, dimethylformamide, dimethyl sulfoxide, acetone, methylene chloride, methanol and other non-hydrogen-donating solvents may be used either alone or in combination as a cosolvent to dissolve the α-methyl-γ-keto acid ester. For example, in the case of using an alkali metal salt of formic acid, the reaction may be performed in a two-phase system where water is used as a cosolvent in combination with an organic solvent to dissolve the alkali metal salt of formic acid. In this case, a phase-transfer catalyst may also be used to accelerate the reaction.

The amount of the ruthenium complex to be used as a catalyst is selected such that the molar ratio (S/C) of the substrate, i.e., the α-methyl-γ-keto acid ester (S) relative to ruthenium metal atoms (C) is in the range of 10 to 1000000, preferably 100 to 15000.

As to the amount of the hydrogen donor relative to the α-methyl-γ-keto acid ester, it is usually used in an equimolar amount or more. When the hydrogen donor is formic acid or an alkali metal salt thereof, it is preferably used in 1.0-fold molar excess or more and used in the range of 20-fold molar excess or less, preferably 10-fold molar excess or less. On the other hand, when the hydrogen donor is isopropanol, etc, it is used in a large excess amount (10-fold molar excess or more) relative to the α-methyl-γ-keto acid ester in terms of reaction equilibrium, and usually used in the range of 1000-fold molar excess or less.

The reaction temperature is selected from the range of 0° C. to 100° C., preferably 0° C. to 70° C.

The reaction pressure is not limited in any way, and it is usually 0.05 to 0.2 MPa, preferably under normal pressure.

The reaction time will vary depending on the catalyst ratio, but it is 1 to 100 hours, usually 2 to 90 hours.

In a second case, step E) is intended for asymmetric hydrogenation reaction of the α-methyl-γ-keto acid ester obtained in step B-2) under basic conditions and in the presence of an optically active ruthenium complex represented by formula (8) and a hydrogen gas to thereby obtain a compound represented by formula (a):

[Formula 58]

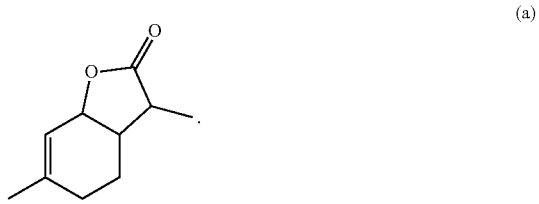

(a)

Explanation will be given below for the optically active ruthenium complex represented by formula (8).

The optically active ruthenium complex represented by formula (8) is as follows:

[Formula 59]

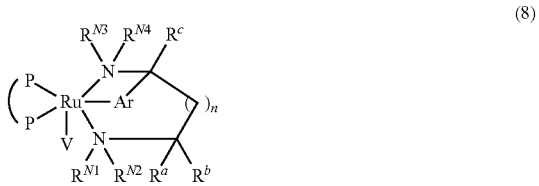

(8)

[wherein P⌒P represents an optically active diphosphine,
V is an anionic group,
$R^a$, $R^b$ and $R^c$ are each independently a hydrogen atom, an optionally substituted $C_1$ to $C_{20}$ alkyl group, an optionally substituted $C_2$ to $C_{20}$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclyl group, or alternatively, $R^b$ and $R^c$ may together form an alkylene group or an alkylenedioxy group, $R^{N1}$, $R^{N2}$, $R^{N3}$ and $R^{N4}$ are each independently a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$ and $R^{N4}$ is a hydrogen atom, and $R^{N1}$ and $R^a$ may together form an alkylene group, n is an integer of 0 to 3, and Ar is an optionally substituted arylene group].

Among candidates for the optically active ruthenium complex represented by formula (8), preferred is an optically active ruthenium complex represented by formula (9) shown below:

[Formula 60]

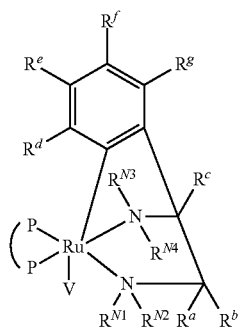

(9)

[wherein p⌒p represents an optically active diphosphine,

V is an anionic group, $R^a$, $R^b$ and $R^c$ are each independently a hydrogen atom, an optionally substituted $C_1$ to $C_{20}$ alkyl group, an optionally substituted $C_2$ to $C_{20}$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclyl group, or alternatively, $R^b$ and $R^c$ may together form an alkylene group or an alkylenedioxy group, $R^d$, $R^e$, $R^f$ and $R^g$ are each independently a hydrogen atom, an optionally substituted alkyl group containing 1 to 20 carbon atoms, an optionally substituted halogenated alkyl group containing 1 to 5 carbon atoms, a halogen atom, an optionally substituted aryl group, an optionally substituted $C_3$ to $C_8$ cycloalkyl group, an optionally substituted tri-substituted silyl group, or an optionally substituted alkoxy group containing 1 to 20 carbon atoms, $R^{N1}$, $R^{N2}$, $R^{N3}$ and $R^{N4}$ are each independently a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$ and $R^{N4}$ is a hydrogen atom, and $R^{N1}$ and $R^a$ may together form an alkylene group].

Among candidates for the optically active ruthenium complexes represented by formulae (8) and (9), more preferred is an optically active ruthenium complex represented by formula (10) shown below:

[Formula 61]

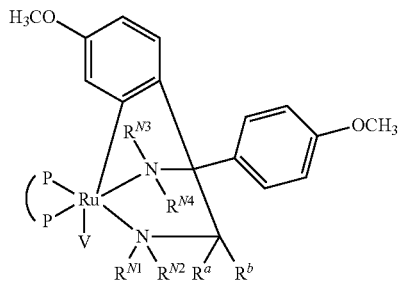

(10)

[wherein p⌒p represents an optically active diphosphine,

V is an anionic group, $R^a$ and $R^b$ are each independently a hydrogen atom, an optionally substituted $C_1$ to $C_{20}$ alkyl group, an optionally substituted $C_2$ to $C_{20}$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclyl group, $R^{N1}$, $R^{N2}$, $R^{N3}$ and $R^{N4}$ are each independently a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$ and $R^{N4}$ is a hydrogen atom, and $R^{N1}$ and $R^a$ may together form an alkylene group].

In the optically active ruthenium complex represented by formula (8), examples of the optionally substituted arylene group represented by Ar include monocyclic, polycyclic or condensed cyclic divalent arylene groups containing 6 to 36 carbon atoms, preferably 6 to 18 carbon atoms, more preferably 6 to 12 carbon atoms, as well as monocyclic, polycyclic or condensed cyclic divalent heteroarylene groups having a 3- to 8-membered, preferably 5- to 8-membered ring containing 1 to 4, preferably 1 to 3, more preferably 1 or 2 heteroatoms selected from a nitrogen atom, an oxygen atom and a sulfur atom. Preferred examples of such arylene groups include a phenylene group, a naphthalenediyl group, a pyridinediyl group, a thiophenediyl group, a furandiyl group and so on, with a phenylene group being particularly preferred. The divalent arylene group may use any position for its attachment, preferably uses adjacent two carbon atoms (ortho position).

Moreover, possible substituents on the above arylene group include a linear or branched alkyl group, a linear or branched alkoxy group, a cycloalkyl group, a halogen atom, an aryl group, a heteroaryl group, and a tri-substituted silyl group, etc.

Explanation will be given below for these substituents on the arylene group.

Examples of a linear or branched alkyl group include linear or branched alkyl groups containing 1 to 10 carbon atoms, preferably 1 to 6 carbon atoms, more preferably 1 to 4 carbon atoms. Such an alkyl group may be substituted with a halogen atom such as a fluorine atom, etc. Specific examples include a methyl group, an ethyl group, a n-propyl group, an isopropyl group, a n-butyl group, an isobutyl group, a s-butyl group, a t-butyl group, a trifluoromethyl group, etc.

Examples of a linear or branched alkoxy group include linear or branched alkoxy groups containing 1 to 10 carbon atoms, preferably 1 to 6 carbon atoms, more preferably 1 to 4 carbon atoms. Specific examples include a methoxy group, an ethoxy group, a n-propoxy group, an isopropoxy group, a n-butoxy group, a s-butoxy group, an isobutoxy group and a t-butoxy group, etc.

Examples of a cycloalkyl group include saturated or unsaturated monocyclic, polycyclic or condensed cyclic cycloalkyl groups containing 3 to 15 carbon atoms, preferably 5 to 7 carbon atoms. Specific examples include a cyclopentyl group, a cyclohexyl group, etc. These cycloalkyl groups may be substituted on their ring with one or two or more alkyl groups containing 1 to 4 carbon atoms or alkoxy groups containing 1 to 4 carbon atoms.

Examples of a halogen atom include a chlorine atom, a bromine atom, a fluorine atom, etc.

Examples of an aryl group include aryl groups containing 6 to 14 carbon atoms. Specific examples include a phenyl group, a naphthyl group, an anthryl group, a phenanthryl group and a biphenyl group, etc. These aryl groups may have one or two or more substituents, including alkyl groups containing 1 to 4 carbon atoms and alkoxy groups containing 1 to 4 carbon atoms as mentioned above.

Examples of a heteroaryl group include 5- or 6-membered cyclic groups containing an oxygen atom, a sulfur atom, a nitrogen atom, etc. Specific examples include a furyl group, a thienyl group, a pyridyl group, etc.

Examples of a tri-substituted silyl group include silyl groups substituted at three positions with alkyl groups or aryl groups as listed above, as exemplified by a trimethylsilyl group, a triethylsilyl group, a triisopropylsilyl group, a tert-butyldimethylsilyl group, a diphenylmethylsilyl group, a dimethylphenylsilyl group, etc.

In formulae (8), (9) and (10), examples of the anionic group represented by V include a hydride ion ($H^-$); a halogen ion such as a chlorine ion ($Cl^-$), a bromine ion ($Br^-$), or an iodine ion ($I^-$); as well as complex anions such as $BH_4$, $BF_4$, $BPh_4$, $PF_6$, an acetoxy group (OAc), a trifluoromethanesulfonyloxy group (OTf), etc. Among them, preferred is a halogen ion.

Explanation will be given below for the groups represented by $R^a$, $R^b$, $R^c$, $R^d$, $R^e$, $R^f$, $R^g$, $R^{N1}$, $R^{N2}$, $R^{N3}$ and $R^{N4}$ in formulae (8), (9) and (10).

Examples of a $C_1$ to $C_{20}$ alkyl group include linear or branched alkyl groups containing 1 to 20 carbon atoms, preferably 1 to 5 carbon atoms, more preferably 1 to 4 carbon atoms, as exemplified by a methyl group, an ethyl group, a n-propyl group, an isopropyl group, a n-butyl group, an isobutyl group, a sec-butyl group, a t-butyl group, a n-pentyl group, a n-hexyl group, a decyl group, a dodecyl group, a hexadecyl group, etc.

Examples of a $C_2$ to $C_{20}$ alkenyl group include linear or branched alkenyl groups containing 2 to 20 carbon atoms, preferably 2 to 10 carbon atoms, more preferably 2 to 6 carbon atoms, as exemplified by an ethenyl group, a n-propenyl group, an isopropenyl group, a 1-butenyl group, a 1-buten-2-yl group, a pentenyl group, a hexenyl group, etc.

Examples of a $C_1$ to $C_{20}$ alkoxy group include groups having oxygen atoms attached to alkyl groups containing 1 to 20 carbon atoms as listed above, as exemplified by a methoxy group, an ethoxy group, a n-propoxy group, an isopropoxy group, a n-butoxy group, a s-butoxy group, an isobutoxy group and a t-butoxy group, etc.

Examples of a halogenated alkyl group containing 1 to 5 carbon atoms include a trifluoromethyl group, a pentafluoroethyl group, a heptafluoropropyl group, a trichloromethyl group, etc.

Examples of a $C_3$ to $C_8$ cycloalkyl group include saturated or unsaturated monocyclic, polycyclic or condensed cyclic cycloalkyl groups containing 3 to 8 carbon atoms, preferably 5 to 7 carbon atoms, as exemplified by a cyclopentyl group, a cyclohexyl group, etc.

Examples of a halogen atom include a chlorine atom, a bromine atom, a fluorine atom, etc.

Examples of a tri-substituted silyl group include silyl groups substituted at three positions with alkyl groups or aryl groups as listed above, as exemplified by a trimethylsilyl group, a triethylsilyl group, a triisopropylsilyl group, a tert-butyldimethylsilyl group, a diphenylmethylsilyl group, a dimethylphenylsilyl group, etc.

Examples of a $C_7$ to $C_{20}$ aralkyl group include aralkyl groups containing 7 to 20 carbon atoms, preferably 7 to 15 carbon atoms or 7 to 10 carbon atoms, which are obtained by attaching alkyl groups containing 1 to 19 carbon atoms as listed above to monocyclic, polycyclic or condensed cyclic aryl groups containing 6 to 20 carbon atoms, preferably 6 to 14 carbon atoms, as exemplified by a benzyl group, an α-methylbenzyl group, an α,α-dimethylbenzyl group, a 2-phenylethyl group, a 3-phenylpropyl group, etc.

Moreover, possible substituents on the above $C_1$ to $C_{20}$ alkyl groups, $C_2$ to $C_{20}$ alkenyl groups, $C_1$ to $C_{20}$ alkoxy groups, halogenated alkyl groups, $C_3$ to $C_8$ cycloalkyl groups, tri-substituted silyl groups and $C_7$ to $C_{20}$ aralkyl groups include linear or branched alkyl groups, linear or branched alkoxy groups, cycloalkyl groups, halogen atoms, aryl groups and tri-substituted silyl groups as mentioned above, etc.

Examples of an aryl group in the optionally substituted aryl group include monocyclic, polycyclic or condensed cyclic aryl groups containing 6 to 20 carbon atoms, preferably 6 to 14 carbon atoms or 6 to 12 carbon atoms. Specific examples include a phenyl group, a naphthyl group, an anthryl group, a phenanthryl group, a biphenyl group and so on, with a phenyl group being preferred. These aryl groups may have one or two or more substituents, including alkyl groups containing 1 to 4 carbon atoms such as a methyl group, an isopropyl group and a t-butyl group, as well as alkoxy groups containing 1 to 4 carbon atoms such as a methoxy group, an ethoxy group, a n-propoxy group, an isopropoxy group, a n-butoxy group, an isobutoxy group, a s-butoxy group and a t-butoxy group, as mentioned above.

Examples of an optionally substituted heterocyclyl group include saturated or unsaturated 5- or 6-membered cyclic groups containing an oxygen atom, a sulfur atom, a nitrogen atom, etc. Specific examples include a furyl group, a thienyl group, a pyridyl group, etc. These heterocyclyl groups may have one or two or more substituents, including alkyl groups containing 1 to 4 carbon atoms such as a methyl group, an isopropyl group and a t-butyl group, as well as alkoxy groups containing 1 to 4 carbon atoms such as a methoxy group, an ethoxy group, a n-propoxy group, an isopropoxy group, a n-butoxy group, an isobutoxy group, a s-butoxy group and a t-butoxy group, as mentioned above.

Example of the alkylene group formed by $R^b$ and $R^c$ include linear or branched alkylene groups containing 1 to 6 carbon atoms, preferably 1 to 4 carbon atoms, as exemplified by a methylene group, an ethylene group, a trimethylene group, a propylene group, a tetramethylene group, etc. These alkylene groups may be substituted with an alkyl group containing 1 to 4 carbon atoms and/or an alkoxy group containing 1 to 4 carbon atoms Examples of the alkylenedioxy group formed by $R^b$ and $R^c$ include linear or branched alkylenedioxy groups containing 1 to 6 carbon atoms, preferably 1 to 4 carbon atoms, as exemplified by a methylenedioxy group, an ethylenedioxy group, a trimethylenedioxy group, etc.

Examples of the alkylene group formed by $R^{N1}$ and $R^a$ include linear or branched alkylene groups containing 1 to 6 carbon atoms, preferably 1 to 4 carbon atoms, as exemplified by a methylene group, an ethylene group, a trimethylene group, a propylene group, a tetramethylene group, etc. These alkylene groups may be substituted with an alkyl group containing 1 to 4 carbon atoms and/or an alkoxy group containing 1 to 4 carbon atoms.

In formulae (8), (9) and (10) of the present invention, the optically active diphosphine (also referred to as bisphosphine) represented by P⌒P is not limited in any way, as long as it is a diphosphine capable of coordinating to ruthenium. Examples include those represented by formula (11) shown below:

$$R^{41}R^{42}P\text{-}T\text{-}PR^{43}R^{44} \quad (11)$$

(wherein $R^{41}$, $R^{42}$, $R^{43}$ and $R^{44}$ are each independently an optionally substituted aryl group, an optionally substituted cycloalkyl group, or an optionally substituted alkyl group, or alternatively, $R^{41}$ and $R^{42}$ may together form a ring and/or $R^{43}$ and $R^{44}$ may together form a ring, and T is an optionally substituted divalent arylene group, an optionally substituted biphenyldiyl group, an optionally substituted binaphthalenediyl group, an optionally substituted bipyridinediyl group, an optionally substituted paracyclophanediyl group, or an optionally substituted ferrocenediyl group).

In formula (11), examples of an aryl group in the optionally substituted aryl group represented by $R^{41}$, $R^{42}$, $R^{43}$ or $R^{44}$ include aryl groups containing 6 to 14 carbon atoms. Specific examples include a phenyl group, a naphthyl group, an anthryl group, a phenanthryl group, a biphenyl group, etc.

These aryl groups may have one or two or more substituents, including an alkyl group, an alkoxy group, etc.

Examples of an alkyl group as a substituent on the aryl group include linear or branched alkyl groups, for example, containing 1 to 15 carbon atoms, preferably 1 to 10 carbon atoms, more preferably 1 to 6 carbon atoms. Specific examples include a methyl group, an ethyl group, a n-propyl group, an isopropyl group, a n-butyl group, a s-butyl group, an isobutyl group and a t-butyl group, etc.

Examples of an alkoxy group as a substituent on the above aryl group include linear or branched alkoxy groups, for example, containing 1 to 6 carbon atoms. Specific examples include a methoxy group, an ethoxy group, a n-propoxy group, an isopropoxy group, a n-butoxy group, a s-butoxy group, an isobutoxy group and a t-butoxy group, etc.

Examples of a cycloalkyl group in the optionally substituted cycloalkyl group represented by $R^{41}$, $R^{42}$, $R^{43}$ or $R^{44}$ include 5- or 6-membered cycloalkyl groups. Preferred examples of such a cycloalkyl group include a cyclopentyl group, a cyclohexyl group, etc. These cycloalkyl groups may be substituted on their ring with one or two or more substituents including alkyl groups or alkoxy groups as listed above for possible substituents on the aryl group.

Examples of an alkyl group in the optionally substituted alkyl group represented by $R^{41}$, $R^{42}$, $R^{43}$ or $R^{44}$ include linear or branched alkyl groups, for example, containing 1 to 15 carbon atoms, preferably 1 to 10 carbon atoms, more preferably 1 to 6 carbon atoms. Specific examples include a methyl group, an ethyl group, a n-propyl group, an isopropyl group, a n-butyl group, a s-butyl group, an isobutyl group and a t-butyl group, etc. These alkyl groups may be substituted with one or two or more substituents including alkoxy groups as listed above for possible substituents on the aryl group.

The ring which may be formed by $R^{41}$ and $R^{42}$ and/or by $R^{43}$ and $R^{44}$ may be a 4-, 5- or 6-membered ring, in which the phosphorus atoms to which $R^{41}$, $R^{42}$, $R^{43}$ and $R^{44}$ are attached are contained as ring members. Specific examples of such a ring include a phosphetane ring, a phosphorane ring, a phosphane ring, a 2,4-dimethylphosphetane ring, a 2,4-diethylphosphetane ring, a 2,5-dimethylphosphorane ring, a 2,5-diethylphosphorane ring, a 2,6-dimethylphosphane ring, a 2,6-diethylphosphane ring, etc. These rings may be in their optically active form.

Candidates for T include an optionally substituted divalent arylene group, an optionally substituted biphenyldiyl group, an optionally substituted binaphthalenediyl group, an optionally substituted bipyridinediyl group, an optionally substituted paracyclophanediyl group, and an optionally substituted ferrocenediyl group, etc.

Examples of a divalent arylene group include those derived from the aryl groups described above for $R^{41}$ to $R^{44}$. Preferred examples of such arylene groups include phenylene groups, as exemplified by o- and m-phenylene groups. Possible substituents on these arylene groups include an alkyl group containing 1 to 6 carbon atoms such as a methyl group, an ethyl group, a n-propyl group, an isopropyl group, a n-butyl group, a s-butyl group, an isobutyl group or a t-butyl group; an alkoxy group containing 1 to 6 carbon atoms such as a methoxy group, an ethoxy group, a n-propoxy group, an isopropoxy group, a n-butoxy group, a s-butoxy group, an isobutoxy group or a t-butoxy group; a hydroxyl group; an amino group; or a substituted amino group, etc.

Preferred biphenyldiyl, binaphthalenediyl and bipyridinediyl groups are those of 1,1'-biaryl-2,2'-diyl structure having an axially chiral structure. Possible substituents on these biphenyldiyl, binaphthalenediyl and bipyridinediyl groups include the groups listed as substituents on the above divalent arylene group, as well as alkylenedioxy groups such as a methylenedioxy group, an ethylenedioxy group, a trimethylenedioxy group, etc., by way of example.

Possible substituents on the paracyclophanediyl and ferrocenediyl groups include the groups described as substituents on the above biphenyldiyl group.

These substituted amino groups include amino groups substituted with one or two or more alkyls containing 1 to 6 carbon atoms.

Specific examples of the optically active diphosphine represented by formula (11) include known optically active diphosphines. One of preferred examples is a compound represented by formula (12) shown below:

[Formula 62]

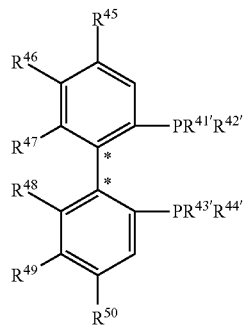

(12)

[wherein * represents an asymmetric carbon atom, $R^{41'}$, $R^{42'}$, $R^{43'}$ and $R^{44'}$ are each independently a phenyl group which may be substituted with a substituent selected from the group consisting of an alkyl group containing 1 to 4 carbon atoms and an alkoxy group containing 1 to 4 carbon atoms; a cyclopentyl group which may be substituted with a substituent selected from the group consisting of an alkyl group containing 1 to 4 carbon atoms and an alkoxy group containing 1 to 4 carbon atoms; or a cyclohexyl group which may be substituted with a substituent selected from the group consisting of an alkyl group containing 1 to 4 carbon atoms and an alkoxy group containing 1 to 4 carbon atoms, $R^{45}$, $R^{46}$, $R^{47}$, $R^{48}$, $R^{49}$ and $R^{50}$ are each independently a hydrogen atom, an alkyl group containing 1 to 4 carbon atoms, an alkoxy group containing 1 to 4 carbon atoms, a halogen atom, a halogenated alkyl group containing 1 to 4 carbon atoms, or a dialkylamino group, two of $R^{45}$, $R^{46}$ and $R^{47}$ together form an optionally substituted alkylene group; an optionally substituted alkylenedioxy group; or an optionally substituted aromatic ring, two of $R^{48}$, $R^{49}$ and $R^{50}$ may together form an optionally substituted alkylene group; an optionally substituted alkylenedioxy group; or an optionally substituted aromatic ring, and $R^{47}$ and $R^{48}$ may together form an optionally substituted alkylene group; an optionally substituted alkylenedioxy group; or an optionally substituted aromatic ring, provided that $R^{47}$ and $R^{48}$ are not hydrogen atoms].

In formula (12), specific examples of an alkyl group containing 1 to 4 carbon atoms include a methyl group, an ethyl group, a n-propyl group, an isopropyl group, a n-butyl group, an isobutyl group, a s-butyl group, a t-butyl group, etc.

Specific examples of an alkoxy group containing 1 to 4 carbon atoms include a methoxy group, an ethoxy group, a n-propoxy group, an isopropoxy group, a n-butoxy group, a s-butoxy group, an isobutoxy group and a t-butoxy group, etc.

Examples of a halogen atom include a chlorine atom, a bromine atom, a fluorine atom, etc.

Examples of a halogenated alkyl group containing 1 to 4 carbon atoms include a trifluoromethyl group, a pentafluoroethyl group, a heptafluoropropyl group, a trichloromethyl group, etc.

Examples of a dialkylamino group include an amino group substituted with the above alkyl groups.

Examples of the alkylene group formed by two of $R^{45}$, $R^{46}$ and $R^{47}$ or by two of $R^{48}$, $R^{49}$ and $R^{50}$ include linear or branched alkylene groups containing 1 to 6 carbon atoms, preferably 1 to 4 carbon atoms, as exemplified by a methylene group, an ethylene group, a trimethylene group, a propylene group, a tetramethylene group, etc. Possible substituents on these alkylene groups include an alkyl group containing 1 to 4 carbon atoms, an alkoxy group containing 1 to 4 carbon atoms, etc.

Examples of the alkylenedioxy group formed by two of $R^{45}$, $R^{46}$ and $R^{47}$ or by two of $R^{48}$, $R^{49}$ and $R^{50}$ include linear or branched alkylenedioxy groups containing 1 to 6 carbon atoms, preferably 1 to 4 carbon atoms, as exemplified by a methylenedioxy group, an ethylenedioxy group, a trimethylenedioxy group, etc. Possible substituents on these alkylenedioxy groups include an alkyl group containing 1 to 4 carbon atoms, an alkoxy group containing 1 to 4 carbon atoms, etc.

Examples of the aromatic ring formed by two of $R^{45}$, $R^{46}$ and $R^{47}$ or by two of $R^{48}$, $R^{49}$ and $R^{50}$ include 6-membered aromatic rings formed together with adjacent atoms. Possible substituents on these aromatic rings include an alkyl group and an alkoxy group, etc.

Preferred examples of formula (12) include those in which $R^{41'}$, $R^{42'}$, $R^{43'}$ and $R^{44'}$ are each independently a phenyl group which may be substituted with one or more substituents selected from the group consisting of an alkyl group containing 1 to 4 carbon atoms and an alkoxy group containing 1 to 4 carbon atoms, $R^{46}$ and $R^{47}$ together form a tetramethylene group; a methylenedioxy group which may be substituted with an alkyl group containing 1 to 4 carbon atoms or a fluorine atom; or a benzene ring together with their adjacent carbon atoms, and $R^{48}$ and $R^{49}$ together form a tetramethylene group; a methylenedioxy group which may be substituted with an alkyl group containing 1 to 4 carbon atoms or a fluorine atom; or a benzene ring together with their adjacent carbon atoms.

More preferred examples of the optically active diphosphine represented by formula (12) include those represented by formula (13) or (14) shown below.

[Formula 63]

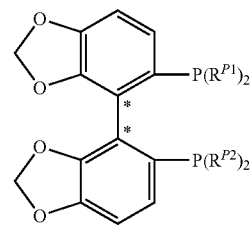

(13)

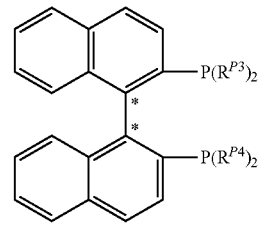

(14)

Specific examples of $R^{P1}$ and $R^{P2}$ in formula (13) as well as $R^{P3}$ and $R^{P4}$ in formula (14) include a phenyl group, a p-tolyl group, a m-tolyl group, an o-tolyl group, a 3,5-xylyl group, a 3,5-di-t-butylphenyl group, a p-t-butylphenyl group, a p-methoxyphenyl group, a 3,5-di-t-butyl-4-methoxyphenyl group, a p-chlorophenyl group, a m-chlorophenyl group, a p-fluorophenyl group, a m-fluorophenyl group, etc. Among them, preferred is a 3,5-xylyl group.

Among candidate compounds for the optically active ruthenium complex represented by formula (10), preferred are those in which P⌒P is the optically active diphosphine represented by formula (14), V is a halogen ion, $R^a$ and $R^b$ are each independently a hydrogen atom or an optionally substituted $C_1$ to $C_{20}$ alkyl group, and $R^{N1}$, $R^{N2}$, $R^{N3}$ and $R^{N4}$ are each a hydrogen atom.

In particular, among candidates for the optically active ruthenium complex represented by formula (10), preferred is the compound shown below. In the following compound, Me represents a methyl group.

[Formula 57]

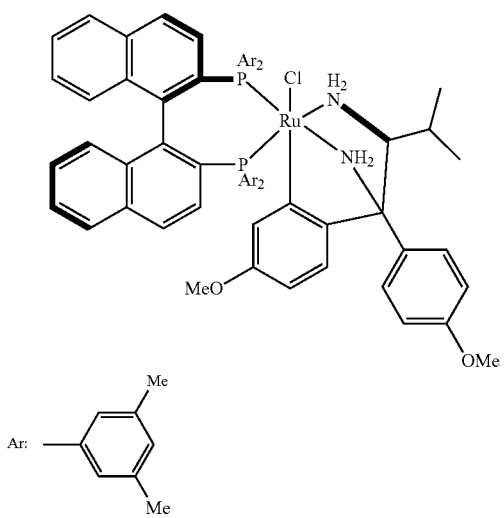

The optically active ruthenium complexes represented by formulae (8), (9) and (10) can be produced according to the procedures described in J. Am. Chem. Soc., 2011, 133, 10696-10699, JP 2011-246435 A and WO2011/135753 A1. Alternatively, commercially available products may be used. Examples include (R)-RUCY™-XylBINAP and (S)-RUCY™-XylBINAP, which are commercially available from STREM Inc.

Although the amount of the optically active ruthenium complex represented by formula (8) to be used will vary depending on the type of reaction vessel, the mode of reaction or the degree of cost-effectiveness, it may be used at a molar ratio ranging from 1/10 to 1/100,000, preferably 1/50 to 1/10,000, relative to the reaction substrate, i.e., the α-methyl-γ-keto acid ester represented by formula (5).

Examples of a base used for this purpose include alkali metal or alkaline earth metal salts such as potassium carbonate ($K_2CO_3$), potassium hydroxide (KOH), lithium hydroxide (LiOH), potassium methoxide ($KOCH_3$), potassium isopropoxide ($KOCH(CH_3)_2$), potassium tert-butoxide ($KOC(CH_3)_3$), lithium methoxide ($LiOCH_3$), potassium naphthalene ($KC_{10}H_8$), lithium isopropoxide ($LiOCH(CH_3)_2$); as well as quaternary ammonium salts, etc. Among them, preferred are alkali metal or alkaline earth metal salts.

The amount of a base to be used is 0.001 to 10 molar equivalents, preferably 0.01 to 2 molar equivalents, relative to the α-methyl-γ-keto acid ester represented by formula (5).

The reaction may preferably be performed in the presence or absence of a solvent, preferably in the presence of a solvent. Solvents preferred for use are those capable of dissolving the substrate and catalyst, which may be used either alone or as a mixture. Specific examples include aromatic hydrocarbons such as toluene and xylene; aliphatic hydrocarbons such as hexane and heptane; halogenated hydrocarbons such as methylene chloride and chlorobenzene; ethers such as diethyl ether, tetrahydrofuran, methyl tert-butyl ether and cyclopentyl methyl ether; alcohols such as methanol, ethanol, 2-propanol, n-butyl alcohol, 2-butanol and tert-butyl alcohol; as well as polyhydric alcohols such as ethylene glycol, propylene glycol, 1,2-propanediol and glycerine. Among them, preferred are ethers or alcohols, and particularly preferred solvents include tetrahydrofuran, methanol, ethanol or 2-propanol. The amount of a solvent to be used may be selected as appropriate, depending on reaction conditions, etc. The reaction is optionally performed under stirring.

The reaction temperature is preferably 0° C. to 100° C., and more preferably is in the range of 0° C. to 50° C. Too low reaction temperatures may increase the residual amounts of unreacted starting materials, while too high reaction temperatures may cause decomposition of the starting materials, catalyst, etc. Thus, too low or high temperatures are not favorable.

Although the reaction successfully proceeds under normal pressure due to the extremely high activity of this catalyst system, the pressure of hydrogen is preferably 0.1 MPa to 10 MPa, more preferably 0.1 MPa to 6 MPa, even more preferably 0.1 MPa to 3 MPa.

The reaction time is 1 minute to 72 hours, preferably 30 minutes to 48 hours.

In step E), when a ruthenium complex selected from the compounds represented by formula (6) or (7) is used to cause reduction reaction or when the optically active ruthenium complex represented by formula (8) is used to cause asymmetric hydrogenation reaction, it is possible to obtain wine lactone in a highly selective manner under normal reaction conditions without using any harmful or expensive reagents.

As described above, in the third embodiment, the compound represented by formula (a) can be produced in a simple manner when a ruthenium complex selected from the compounds represented by formula (6) or (7) is used to cause reduction reaction or when the optically active ruthenium complex represented by formula (8) is used to cause asymmetric hydrogenation reaction in step E) following step B-2).

In particular, in step E), when an optically active form of the ruthenium complex represented by formula (6) or (7) is used to cause asymmetric reduction reaction or when the optically active ruthenium complex represented by formula (8) is used to cause asymmetric hydrogenation reaction, the (3S,3aS,7aR) and (3R,3aS,7aR) isomers can be produced in a selective manner. In particular, the (3S,3aS,7aR) isomer can be produced in a highly selective manner. When distillation is performed in step D) subsequent to step E), the (3R,3aS,7aR) isomer is isomerized to the (3S,3aS,7aR) isomer, so that wine lactone of (3S,3aS,7aR) form can be produced in a simple and highly selective manner in high optical purity and in high yields.

Step D)

In the production process of the present invention, the compounds obtained in the first, second and third embodiments are further distilled under basic conditions to thereby achieve selective production of a diastereomeric isomer mixture composed of (3S,3aS,7aR) and (3R,3aR,7aS) isomers represented by the following formulae:

[Formula 65]

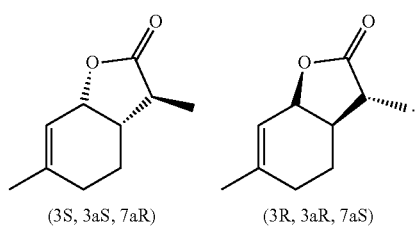

(3S, 3aS, 7aR)    (3R, 3aR, 7aS)

The first, second and third embodiments preferably further comprise the above step (step D)).

Step D) is performed under basic conditions. Examples of a base used in this step include inorganic bases and organic bases, etc. Specific examples of inorganic and organic bases include those listed in step A) of the first embodiment. Among them, preferred are organic bases, especially sodium methoxide and sodium ethoxide.

The amount of a base to be used is selected as appropriate from the range of 0.001 to 10 molar equivalents, preferably 0.01 to 3 molar equivalents, relative to the compound represented by formula (a).

Distillation may be performed under conditions allowing sufficient separation between a diastereomeric isomer mixture composed of (3S,3aS,7aR) and (3R,3aR,7aS) isomers and a diastereomeric isomer mixture composed of (3R,3aS,7aR) and (3S,3aR,7aS) isomers, which are represented by the following formulae:

[Formula 66]

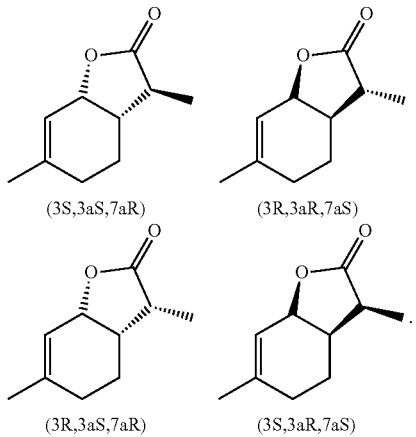

(3S,3aS,7aR)     (3R,3aR,7aS)

(3R,3aS,7aR)     (3S,3aR,7aS)

Since the diastereomeric isomer mixture composed of (3S,3aS,7aR) and (3R,3aR,7aS) isomers and the diastereomeric isomer mixture composed of (3R,3aS,7aR) and (3S,3aR,7aS) isomers have different boiling points, they can be separated from each other based on differences in their boiling points.

For example, the above conditions can be satisfied by using a packed tower or the like for distillation.

Packing materials used for this purpose include Raschig rings, Lessing rings, pall rings, Sulzer packing, etc.

The distillation temperature is preferably equal to or higher than a temperature at which isomerization reaction proceeds on the methyl group at the 3-position of the compound represented by formula (a):

[Formula 67]

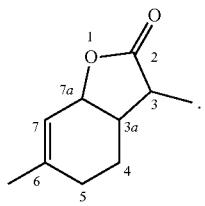

(a)

It is usually 0° C. to 130° C., but is preferably selected as appropriate from the range of 50° C. to 130° C.

Wine lactone, i.e., the (3S,3aS,7aR) isomer is excellent in the quality of aroma, and the intensity of its aroma is also high. For this reason, it is also favorable in terms of cost-effectiveness to selectively produce a diastereomeric isomer mixture composed of (3S,3aS,7aR) and (3R,3aR,7aS) isomers through distillation.

According to a preferred embodiment of the present invention, step D) allows production of compounds represented by formula (a) in which a diastereomeric isomer mixture composed of (3S,3aS,7aR) and (3R,3aR,7aS) isomers constitutes 90% by weight or more of the total weight of the compounds represented by formula (a) obtained in step C), particularly the (3S,3aS,7aR), (3R,3aR,7aS), (3R,3aS,7aR) and (3S,3aR,7aS) isomers.

[Formula 68]

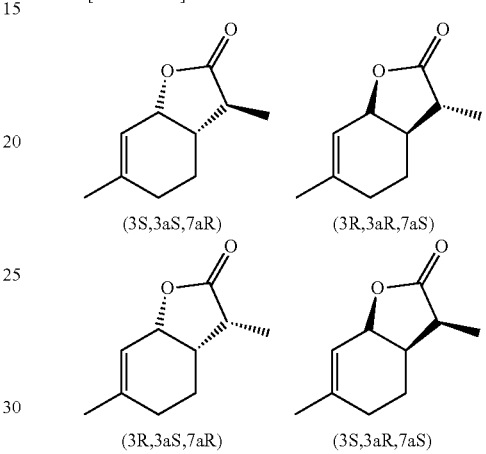

(3S,3aS,7aR)     (3R,3aR,7aS)

(3R,3aS,7aR)     (3S,3aR,7aS)

Moreover, it is possible to produce a diastereomeric isomer mixture composed of (3S,3aS,7aR) and (3R,3aR,7aS) isomers which is enriched for the (3S,3aS,7aR) isomer when step D) is performed after the (3S,3aS,7aR) isomer is selectively produced through asymmetric reduction reaction in the presence of an optically active form of the ruthenium complex represented by formula (6) or (7) and a hydrogen donor during the reduction reaction in step C) of the first or second embodiment; through asymmetric reduction reaction in the presence of an optically active form of the ruthenium complex represented by formula (6) or (7) and a hydrogen donor in step E) of the third embodiment; or through asymmetric hydrogenation reaction in the presence of the optically active ruthenium complex represented by formula (8) and a hydrogen gas in step E) of the third embodiment.

Furthermore, when step D) is performed after asymmetric reduction reaction in the presence of an optically active form of the ruthenium complex represented by formula (6) or (7) and a hydrogen donor in step E) of the third embodiment, it is possible to produce compounds represented by formula (a) in which the (3S,3aS,7aR) isomer constitutes 85% by weight or more of the total weight of the compounds represented by formula (a) obtained in step E), particularly the (3S,3aS,7aR), (3R,3aR,7aS), (3R,3aS,7aR) and (3S,3aR,7aS) isomers.

Step F)

In the case of causing asymmetric reduction reaction in the presence of an optically active form of the ruthenium complex represented by formula (6) or (7) and a hydrogen donor in step C) of the first or second embodiment; causing asymmetric reduction reaction in the presence of an optically active form of the ruthenium complex represented by formula (6) or (7) and a hydrogen donor in step E) of the third embodiment; or causing asymmetric hydrogenation reaction in the presence of the optically active ruthenium complex represented by formula (8) and a hydrogen gas in step E) of the third embodiment, wine lactone of (3S,3aS,7aR) form can be produced in high yields by distillation in the subsequent step D), and the resulting high-yield wine lactone of (3S,3aS,7aR) form may further be purified by recrystallization (step F)) to thereby produce substantially pure wine lactone of (3S,3aS,7aR) form, i.e., highly optically pure wine lactone of (3S,3aS,7aR) form.

Examples of a solvent used in step F) include, but are not particularly limited to, aliphatic hydrocarbons such as pentane, hexane, heptane, octane, decane, and cyclohexane; aromatic hydrocarbons such as benzene, toluene, and xylene; halogenated hydrocarbons such as dichloromethane, chloroform, carbon tetrachloride, and o-dichlorobenzene; ethers such as diethyl ether, diisopropyl ether, tert-butyl methyl ether, dimethoxyethane, ethylene glycol diethyl ether, tetrahydrofuran, 1,4-dioxane, and 1,3-dioxolane; alcohols such as methanol, ethanol, 2-propanol, n-butanol, 2-ethoxyethanol, and benzyl alcohol; polyhydric alcohols such as ethylene glycol, propylene glycol, 1,2-propanediol, and glycerine; acids such as formic acid, acetic acid, and propionic acid; sulfoxides such as dimethyl sulfoxide; as well as N-methylpyrrolidone, water, etc.

These solvents may be used either alone or in combination as appropriate. Among them, preferred are aliphatic hydrocarbons and alcohols.

The amount of a solvent to be used is selected as appropriate from the range of usually 0.5- to 100-fold volume, preferably 1- to 40-fold volume, relative to the diastereomeric isomer mixture composed of (3S,3aS,7aR) and (3R,3aR,7aS) isomers represented by the following formulae:

[Formula 69]

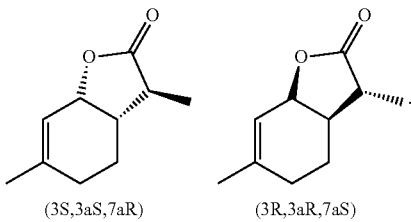

(3S,3aS,7aR)    (3R,3aR,7aS)

The reaction temperature of recrystallization is selected as appropriate from the range of usually 0° C. to 100° C., preferably 0° C. to 80° C. Likewise, the reaction time is selected as appropriate from the range of usually 0.5 to 48 hours, preferably 1 to 24 hours.

As described above, in the present invention, all of the production steps are performed at a temperature of 0° C. or more to 130° C. or less, so that wine lactone or a stereoisomer thereof or a mixture thereof can be produced without requiring extremely low or high temperatures.

Furthermore, wine lactone or a stereoisomer thereof or a mixture thereof can be produced without particularly requiring any purification step by silica gel column chromatography in each of the production steps.

The wine lactone obtained in the present invention or a stereoisomer thereof or a mixture thereof can be added to food and beverage products, perfumery and cosmetics, daily and sundry goods, oral compositions, pharmaceutical preparations, and so on.

Upon addition of wine lactone or a stereoisomer thereof or a mixture thereof to food and beverage products, perfumery and cosmetics, daily and sundry goods, oral compositions, and/or pharmaceutical preparations, these products can be provided with a juicy sensation, a fully-ripened sensation, and/or a full-bodied sensation.

Examples of food and beverage products include beverages such as fruit drinks, fruit liquors, milk beverages, carbonated beverages, soft drinks, and drinkable preparations; frozen desserts such as ice creams, sorbets, and ice lollies; desserts such as jellies and puddings; western confectionery such as cakes, cookies, chocolates, and chewing gums; Japanese confectionery such as manju (sweet bean paste buns), yokan (sweet bean paste jelly), and uiro (sweet rice jelly); jams; candies; bakery products; tea beverages or palatable beverages such as green tea, oolong tea, black tea, persimmon leaf tea, chamomile tea, kumazasa (*Sasa albo-marginata*) tea, mulberry leaf tea, dokudami (*Houttuynia cordata*) tea, pu-erh tea, mate tea, rooibos tea, gymnema tea, guava tea, coffee, and cocoa; soups such as Japanese soups, western soups, and Chinese soups; flavorings and seasonings; various instant beverages or foods; various junk foods, etc.

Examples of perfumery and cosmetics include fragrance products, basic cosmetics, make-up cosmetics, hair cosmetics, sun care cosmetics, medicated cosmetics, etc.

More specifically, examples of fragrance products include perfume, eau de parfum, eau de toilette, eau de cologne, and so on;

examples of basic cosmetics include face wash cream, vanishing cream, cleansing cream, cold cream, massage cream, skin milk, lotion, essence, facial pack, make-up remover, and so on;

examples of make-up cosmetics include foundation, loose powder, compact powder, talcum powder, lipstick, lip pomade, cheek color, eyeliner, mascara, eyeshadow, eyebrow pencil, eye pack, nail enamel, enamel remover, and so on;

examples of hair cosmetics include pomade, brilliantine, setting lotion, hair stick, hair solid, hair oil, hair treatment, hair cream, hair tonic, hair liquid, hair spray, bandoline, hair growth promoter, hair dye, and so on;

examples of sun care cosmetics include suntan products, sunscreen products, and so on; and examples of medicated cosmetics include antiperspirant, after shaving lotion, gel, permanent waving agent, medicated soap, medicated shampoo, medicated skin cosmetics, and so on.

Examples of daily and sundry goods include hair care products, soaps, body cleansers, bath preparations, fabric detergents, soft-finishing agents, detergents, kitchen detergents, bleaching agents, aerosols, air fresheners, sundry goods, shaving products, skin care products, repellents, smoking products, etc.

More specifically, examples of hair care products include shampoo, conditioner, two-in-one shampoo, hair conditioner, hair treatment, hair pack, and so on;

examples of soaps include toilet soap, bath soap, perfumed soap, transparent soap, synthetic soap, and so on;

examples of body cleansers include body wash, body shampoo, hand wash, and so on;

examples of bath preparations include bath additives (e.g., bath salt, bath tablet, bath liquid), foam bath (e.g., bubble bath), bath oil (e.g., bath perfume, bath capsule), milk bath, bath gel, bath cube, and so on;

examples of fabric detergents include heavy fabric detergent, light fabric detergent, liquid detergent, laundry soap, concentrated detergent, powdered soap, and so on;

examples of soft-finishing agents include softener, furniture care, and so on;

examples of detergents include cleanser, household cleaner, toilet detergent, bath detergent, glass cleaner, mold remover, drain detergent, and so on;

examples of kitchen detergents include kitchen soap, kitchen synthetic soap, dish detergent, and so on;

examples of bleaching agents include oxidizing bleaching agents (e.g., chlorine-based bleaching agent, oxygen-based bleaching agent), reducing bleaching agents (e.g., sulfur-based bleaching agent), optical bleaching agents, and so on;

examples of aerosols include those of spray type, powder spray, and so on;

examples of air fresheners include those of solid type, gel type or liquid type, and so on;

examples of sundry goods include tissue paper, toilet paper, and so on;

examples of shaving products include shaving foam, and so on; and examples of skin care products include hand cream, body cream, body lotion, and so on.

Examples of oral compositions include dentifrices, oral washes, mouth washes, troches, chewing gums, etc.

Examples of pharmaceutical preparations include skin preparations for external use (e.g., poultices, ointments), preparations for internal use, etc.

EXAMPLES

The present invention will be further described in more detail by way of the following examples, which are not intended to limit the scope of the present invention.

[Measuring Instruments]

Compounds obtained in the following examples were measured for their properties using the instruments listed below.

(1) NMR: DRX500 (Bruker, Inc.)

(2) GC/MS: GCMS-QP2010 (Shimadzu Corporation, Japan)

Column: RTX-1 (30 m long and 0.25 mm inner diameter, liquid phase thickness: 0.25 μm)

(3) Gas chromatographic purity analysis: GC-4000 (GL Sciences Inc., Japan)

Column: RTX-1 (30 m long and 0.25 mm inner diameter, liquid phase thickness: 0.25 μm)

Temperature conditions: column: 100° C.→250° C. (10° C./minute), inlet: 250° C., detector: 250° C. (FID)

(4) Optical purity analysis (gas chromatography): GC-4000 (GL Sciences Inc., Japan)

Column: Beta DEX™-225 (30 m long and 0.25 mm inner diameter, liquid phase thickness: 0.25 μm)

Temperature conditions: column: 100° C.→200° C. (2° C./minute), inlet: 200° C., detector: 200° C. (FID)

Melting point: YANAGIMOTO MICRO MELTING POINT APPARATUS

In the formulae shown below, Me represents a methyl group.

Example 1

[1] Step A

[Formula 70]

Under a nitrogen stream, 28% sodium methoxide in methanol (577.5 g, 2.99 mol) and methanol (500 ml) were stirred at an internal temperature of 3° C., to which methyl acetoacetate (1-1) (347.6 g, 2.99 mol) was then added dropwise and methyl 2-bromopropionate (2-1) (577.5 g. 2.99 mol, 1 eq) was further added dropwise. After completion of the dropwise addition, the mixture was reacted by being stirred at 70° C. for 3 hours, followed by addition of 0.5 N HCl (350 ml) to stop the reaction. After the solvent was recovered under reduced pressure, the product was extracted with toluene to give 628.5 g of crude 2-aceto-3-methyl-succinic acid ester (3-1), which was further distilled at 120° C. to obtain 460.9 g of 2-aceto-3-methyl-succinic acid ester (3-1).

$^1$H-NMR (CDCl$_3$) (Isomer major): δ 1.17(d, 3H, J=8.9), 2.26(s, 3H), 3.22(m, 1H), 3.65(s, 3H), 3.73(s, 3H), 3.85(d, 1H, J=10.3)

$^1$H-NMR (CDCl$_3$) (Isomer minor): δ 1.15(d, 3H, J=9.0), 2.28(s, 3H), 3.22(m, 1H), 3.67(s, 3H), 3.70(s, 3H), 3.82(d, 1H, J=9.5)

$^{13}$C-NMR (CDCl$_3$): δ 15.07, 15.26, 29.59, 38.68, 38.71, 52.07, 52.58, 52.61, 61.41, 62.01, 168.15, 175.00, 201.27

GC/MS (m/e); 202(M$^+$,), 171, 160, 143, 128, 113, 101, 85, 70, 69, 43, 41, 36

[2] Step B-1

[Formula 71]

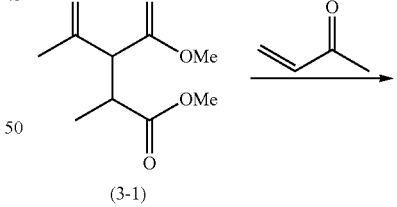

The 2-aceto-3-methyl-succinic acid ester (3-1) obtained in [1] above (250.0 g, 1.24 mol) was dissolved in dimethyl sulfoxide (hereinafter abbreviated as DMSO; 500 ml), to which potassium hydroxide (1.04 g, 0.02 mol) was then added and stirred at an internal temperature of 40° C. for 30 minutes. After methyl vinyl ketone (113 ml, 1.35 mol) was added dropwise at the same temperature, the reaction mixture was stirred at the same temperature for 3 hours. After addition of methanol (500 ml), the reaction mixture was cooled to 0° C. to 10° C., and 28% sodium methoxide in methanol (239.0 g, 1.24 mol) was added dropwise thereto at 0° C. to 10° C. After stirring for 30 minutes, 2 N NaOH (1.58 L, 3.16 mol) was added dropwise, and the reaction mixture was warmed to 40° C. and stirred for 7 hours.

After the solvent was recovered under reduced pressure, the reaction mixture was diluted with 5 N HCl (892 ml, 4.46 mol) and extracted with ethyl acetate, and the organic layer was then concentrated with an evaporator to give 250 g of crude α-methyl-γ-keto acid (4).

$^1$H-NMR (CDCl$_3$) (Isomer major): δ 1.22(d, 3H, J=7.3), 1.98(s, 3H), 2.04(m, 2H), 2.38(m, 2H), 2.63(dt, 1H, J=4.7, 12.5), 2.99(dq, 1H, J=4.5, 7.2), 5.90(s, 1H), 6.22(bs, 1H)

$^1$H-NMR (CDCl$_3$) (Isomer minor): δ 1.11(d, 3H, J=7.2), 1.97(s, 3H), 2.04(m, 2H), 2.38(m, 2H), 2.76(dt, 1H, J=4.9, 14.1), 3.15(dq, 1H, J=5.3, 7.2), 5.89(s, 1H), 6.22(bs, 1H)

$^{13}$C-NMR (CDCl$_3$): δ 12.54, 13.16, 24.21, 25.38, 30.96, 31.24, 37.88, 38.99, 47.81, 48.07, 126.37, 126.43, 162.79, 178.97, 181.25, 198.81, 199.59

GC/MS (m/e); 164(M-H2O,), 136, 123, 109, 95, 82, 67, 54, 39, 36

(3) Step C

[Formula 72]

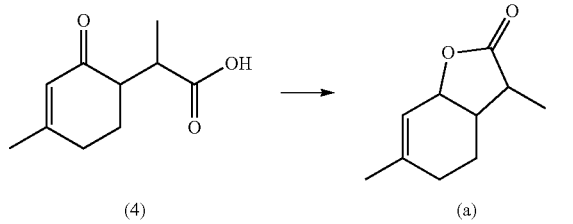

[Preparation of Mixed γ-Keto Acid Sodium Salt-Cerium Chloride Solution]

The crude α-methyl-γ-keto acid (4) obtained in [2] above (130.0 g, 0.45 mol) was dissolved in ethanol (950 ml) and the resulting solution was stirred under a nitrogen atmosphere at 0° C. to 10° C., to which 28% sodium methoxide in methanol (138.4 g, 0.72 mol) and cerium chloride heptahydrate (101.5 g, 0.27 mol) were then added and stirred for 30 minutes to prepare a mixed γ-keto acid sodium salt-cerium chloride solution.

[Reduction Reaction]

Ethanol (1.0 L) was stirred at an internal temperature of 2° C., and sodium borohydride (9.45 g, 0.25 mol) was added thereto. To this mixture, the whole volume of the mixed γ-keto acid sodium salt-cerium chloride solution thus prepared was added dropwise. The mixture was reacted by being further stirred at 0° C. to 10° C. for 1.5 hours, followed by dropwise addition of acetone (102 ml, 1.38 mol), water (2.6 L) and 5 N hydrochloric acid (300 g, 1.50 mol) to stop the reaction.

The solvent was then recovered under reduced pressure, followed by addition of toluene to extract the product. The resulting organic layer was washed with 5% aqueous sodium carbonate and with 5% aqueous sodium chloride. The resulting organic layer was concentrated under reduced pressure to give compound (a) ((3S,3aS,7aR)+(3R,3aR,7aS):(3R,3aS,7aR)+(3S,3aR,7aS)=57:43).

The same procedures as shown in [Preparation of mixed γ-keto acid sodium salt-cerium chloride solution] and [Reduction reaction] above were repeated three times to obtain 194.6 g in total of compound (a).

[4] Step D (Distillation)

To the compound (a) obtained in (3) above (194.6 g, 1.17 mol) ((3S,3aS,7aR)+(3R,3aR,7aS):(3R,3aS,7aR)+(3S,3aR,7aS)=57:43), sodium methoxide was added in 0.03 molar equivalents, followed by precision distillation (100° C. to 130° C.) while allowing isomerization to proceed, thereby obtaining 153.5 g of the purified compound (a) ((3S,3aS,7aR)+(3R,3aR,7aS):(3R,3aS,7aR)+(3S,3aR,7aS)=97:3).

$^1$H-NMR (CDCl$_3$): δ 1.24(d, 3H, J=7.2), 1.71(s, 3H), 1.73 (m, 1H), 1.82(m, 1H), 1.97(m, 2H), 2.25(m, 1H), 2.41(dq, 1H, J=7.2, 8.5), 4.88(m, 1H), 5.49(m, 1H)

$^{13}$C-NMR (CDCl$_3$): δ 13.95, 22.23, 23.59, 25.90, 37.56, 40.32, 75.38, 118.76, 140.72, 179.68

GC/MS (m/e); 166(M$^+$,), 151, 138, 123, 107, 93, 79, 69, 55, 39, 36

Example 2

[1] Step B-2

[Formula 73]

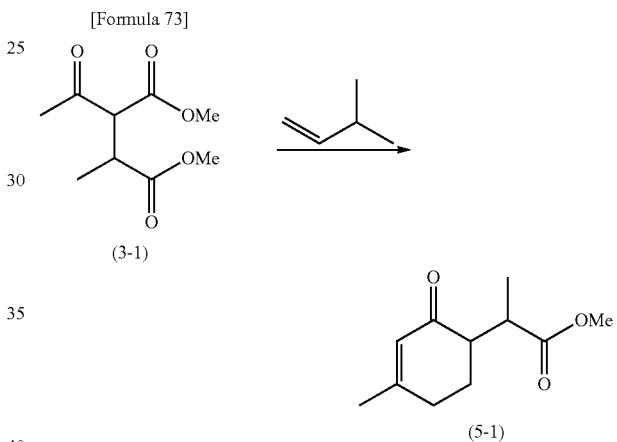

The undistilled crude 2-aceto-3-methyl-succinic acid ester (3-1) obtained in [1]<Step A> of Example 1 (265.0 g, 1.31 mol) was dissolved in DMSO (530 ml), to which potassium hydroxide (1.10 g, 0.02 mol) was then added and stirred at an internal temperature of 40° C. for 30 minutes. After methyl vinyl ketone (120 ml, 1.44 mol) was added dropwise at the same temperature, the mixture was reacted by being stirred at the same temperature for 3 hours. The reaction mixture was cooled to 0° C. to 10° C. and methanol (500 ml) was added thereto, followed by dropwise addition of 28% sodium methoxide in methanol (75.8 g, 0.39 mol) at 0° C. to 10° C. After stirring for 30 minutes, 5 N HCl (78.0 g, 0.39 mol) was added dropwise to neutralize the reaction mixture (pH=6 to 7).

After the solvent was recovered under reduced pressure, anhydrous magnesium chloride (93.5 g, 0.98 mol) was added and heated at 130° C. for 18 hours to cause decarboxylation reaction. The reaction mixture was cooled to room temperature, diluted with water (530 ml) and then extracted with ethyl acetate. The organic layer was concentrated to give 190.5 g of crude α-methyl-γ-keto acid ester (5-1), which was further purified by distillation to obtain 121.9 g of α-methyl-γ-keto acid ester (5-1).

$^1$H-NMR (Isomer major) (CDCl$_3$, σ in ppm) 1.10(3H, d, J=7.2), 1.72-1.76(1H, m), 1.95(3H, s), 1.97-2.05(1H, m), 2.38-2.47(2H, m), 2.72-2.77(1H, m), 3.05-3.10(1H, m), 3.71 (3H, s)

¹H-NMR (Isomer minor) (CDCl₃, σ in ppm) 1.19(3H, d, J=7.2), 1.72-1.76(1H, m), 1.95(3H, s), 1.97-2.05(1H, m), 2.38-2.47(2H, m), 2.55-2.59(1H, m), 2.96-3.02(1H, m), 3.67 (3H, s)

¹³C-NMR (CDCl₃, 500 MHz) 198.83, 198.74, 176.64, 175.27, 161.86, 161.51, 126.47, 126.43, 77.26, 77.00, 76.75, 51.75, 51.64, 48.45, 48.01, 38.48, 38.10, 31.18, 30.75, 25.21, 24.45, 24.12, 24.10, 13.69, 12.93

[2] Step B-3 and Step C

[Formula 74]

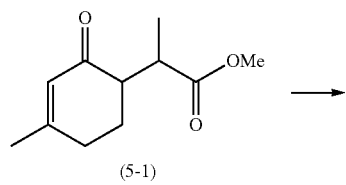

(5-1)

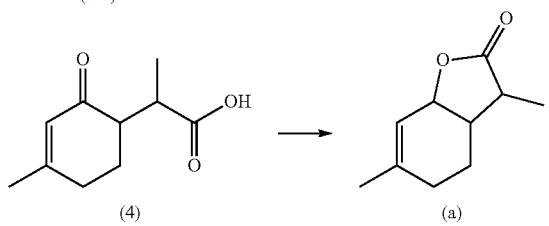

(4)    (a)

<Step B-3>

The α-methyl-γ-keto acid ester (5-1) obtained in [1] above (60.0 g, 0.31 mol) was cooled to 0° C. to 10° C. and 2 N aqueous NaOH (230 ml, 0.46 mol) was added thereto, followed by stirring at room temperature for 1 hour. After 5 N HCl (122 ml) was added dropwise, the product was extracted with ethyl acetate and the resulting organic layer was concentrated to give 51.7 g of α-methyl-γ-keto acid (4).

<Step C>

The α-methyl-γ-keto acid (4) obtained in step B-3 above (51.7 g, 0.284 mol) was dissolved in methanol (500 ml) and cooled to 2° C. 28% Sodium methoxide in methanol (49.4 g, 0.26 mol) and cerium chloride heptahydrate (21.7 g, 0.06 mol) were added and the mixture was further stirred for 30 minutes, to which sodium borohydride (5.5 g, 0.15 mol) was then added. The mixture was reacted by being stirred for 1 hour, followed by addition of acetone (51 ml, 0.69 mol), water (665 ml) and 5 N HCl (107.0 g) to stop the reaction.

After the solvent was recovered under reduced pressure, the product was extracted with toluene, and the resulting organic layer was washed with 5% aqueous sodium carbonate and with 5% aqueous sodium chloride and then concentrated under reduced pressure.

The same procedures as shown in step B-3 and step C above were repeated twice to obtain 72.9 g in total of compound (a) ((3S,3aS,7aR)+(3R,3aR,7aS):(3R,3aS,7aR)+(3S, 3aR,7aS)=58:42).

[3] Step D (Distillation)

To the compound (a) obtained in [2] above (72.9 g, 0.439 mol), sodium methoxide (0.73 g, 0.0135 mol) was added, followed by precision distillation (100° C. to 130° C.) while allowing isomerization to proceed, thereby obtaining 59.4 g of the purified compound ((3S,3aS,7aR)+(3R,3aR,7aS):(3R, 3aS,7aR)+(3S,3aR,7aS)=97:3, yield: 76.8%).

¹H-NMR (CDCl₃): δ 1.24(d, 3H, J=7.2), 1.71(s, 3H), 1.73 (m, 1H), 1.82(m, 1H), 1.97(m, 2H), 2.25(m, 1H), 2.41(dq, 1H, J=7.2, 8.5), 4.88(m, 1H), 5.49(m, 1H)

¹³C-NMR (CDCl₃): δ 13.95, 22.23, 23.59, 25.90, 37.56, 40.32, 75.38, 118.76, 140.72, 179.68

GC/MS (m/e); 166(M⁺,), 151, 138, 123, 107, 93, 79, 69, 55, 39, 36

Example 3

[1] Step C

[Formula 75]

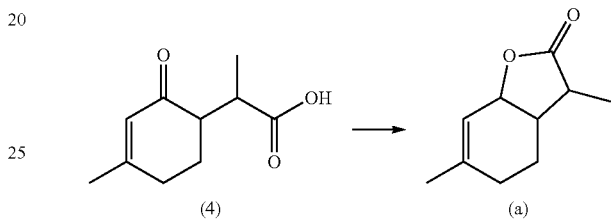

(4)    (a)

The α-methyl-γ-keto acid (4) obtained in [2] <Step B-3> of Example 2 (0.4 g, 0.0022 mol) was dissolved in methanol (4 ml), to which triethylamine (433 mg, 0.00428 mol), the ruthenium complex represented by formula (20) below (14.3 mg, 0.0220 mmol) and formic acid (0.404 ml, 0.0107 mol) were then added and stirred at 60° C. for 20 hours. To this mixture, additional formic acid (0.404 ml, 0.0107 mol) was further added and stirred for 20 hours to cause reaction, thereby giving compound (a).

Then, the degree of conversion was confirmed to be 55%, as measured by gas chromatography. The diastereoselectivity was 56% d.e., and the optical purity of the (3S,3aS,7aR) isomer was 42% ee.

[Formula 76]

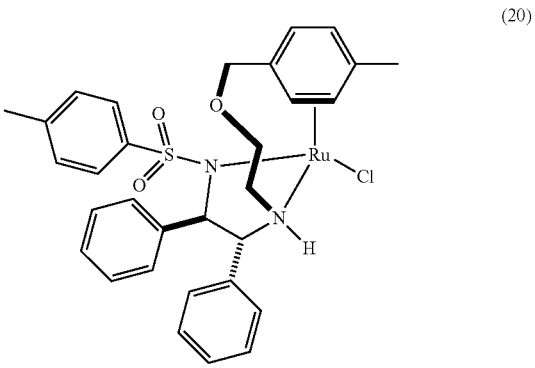

(20)

(R,R)-Ts-DENEB™ (STREM, Inc.)

Example 4

[1] Step C

[Formula 77]

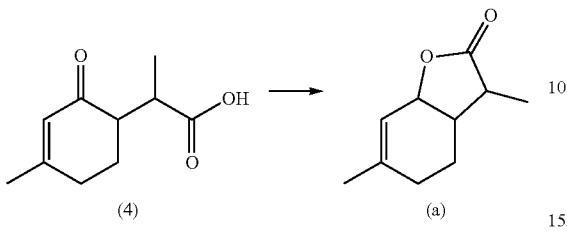

The α-methyl-γ-keto acid (4) obtained in [2] <Step B-3> of Example 2 (0.4 g, 0.0022 mol) was dissolved in methanol (4 ml), to which DABCO (1.64 g, 0.01463 mol), the ruthenium complex represented by formula (20) below (14.3 mg, 0.0220 mmol) and formic acid (0.55 ml, 0.01463 mol) were then added and stirred at 60° C. for 20 hours to cause reaction, thereby giving compound (a).

Then, the degree of conversion was confirmed to be 26%, as measured by gas chromatography. The diastereoselectivity was 36% d.e., and the optical purity of the desired naturally occurring wine lactone, i.e., the (3S,3aS,7aR) isomer was 57% ee.

[Formula 78]

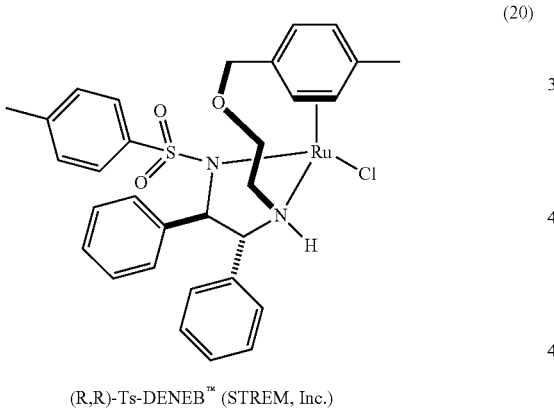

(R,R)-Ts-DENEB™ (STREM, Inc.)

Example 5

[1] Step E

[Formula 79]

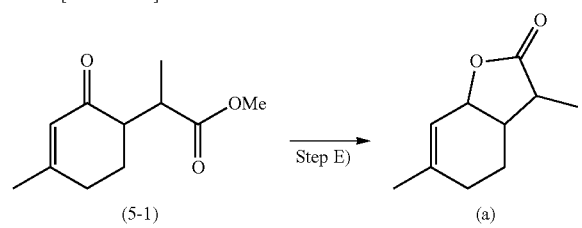

The α-methyl-γ-keto acid ester (5-1) obtained in [1] <Step B-2> of Example 2 (0.4 g, 0.00204 mol) was dissolved in ethanol (4 ml), to which the ruthenium complex represented by formula (21) below (12 mg, 0.0102 mmol) and potassium tert-butoxide (11 mg, 0.102 mmol) were then added and stirred at a hydrogen pressure of 3 MPa at 40° C. for 21 hours to cause reaction, thereby giving compound (a).

Then, the degree of conversion was confirmed to be 9%, as measured by gas chromatography. The diastereoselectivity was 24% d.e., and the optical purity of the (3S,3aS,7aR) isomer was 25% ee.

[Formula 80]

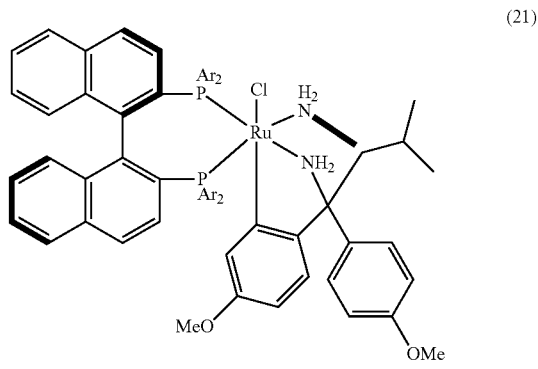

[RuCl(R)-xylbinap][(S)-daipen]

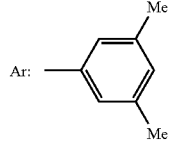

Example 6

[1] Step E

[Formula 81]

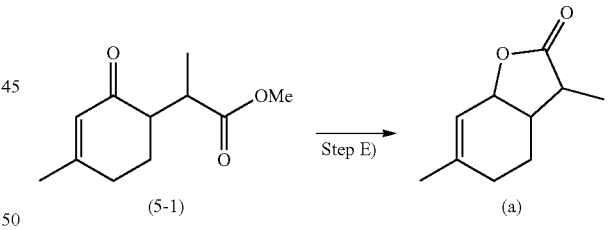

The α-methyl-γ-keto acid ester (5-1) obtained in [1] <Step B-2> of Example 2 (80 g, 0.4076 mol) was dissolved in methanol (200 ml), to which DABCO (45.7 g, 0.4076 mol), the ruthenium complex represented by formula (20) below (2.65 g, 0.004076 mol) and formic acid (15.3 ml, 0.4076 mol) were then added and stirred at 60° C. for 25 hours. To this mixture, additional formic acid (15.3 ml, 0.4076 mol) was further added and stirred for 45 hours to cause reaction.

Then, the reaction mixture was mixed with water (2 ml) and toluene (2 ml) to extract the product, and the resulting organic layer was washed with 5% aqueous sodium carbonate and with 5% aqueous sodium chloride. The resulting organic layer was concentrated under reduced pressure to give 61.7 g of compound (a) ((3S,3aS,7aR)+(3R,3aR,7aS):(3R,3aS, 7aR)+(3S,3aR,7aS)=80:20, (3S,3aS,7aR):(3R,3aR,7aS)=90: 10, optical purity of (3S,3aS,7aR) isomer: 80% ee).

[Formula 82]

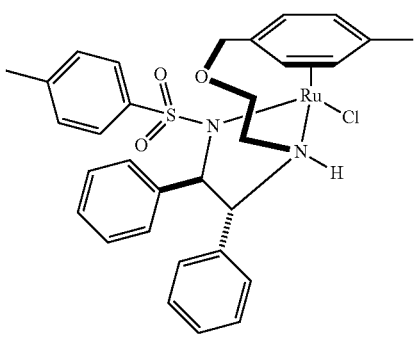

(20) (R,R)-Ts-DENEB™ (STREM, Inc.)

[2] Step D (Distillation)

To the compound (a) obtained in [1] above (61.7 g, 0.3712 mol), sodium methoxide (0.62 g, 0.0111 mol) was added, followed by precision distillation (100° C. to 130° C.) while allowing isomerization to proceed, thereby obtaining 14.7 g of the purified compound (a) ((3S,3aS,7aR):(3R,3aR,7aS) =90:10, (3S,3aS,7aR)+(3R,3aR,7aS):(3R,3aS,7aR)+(3S, 3aR,7aS)=100:0, yield: 22%).

$^1$H-NMR (CDCl$_3$): δ 1.26(d, 3H, J=7.3), 1.73(s, 3H), 1.73 (m, 1H), 1.82(m, 1H), 1.97(m, 2H), 2.25(m, 1H), 2.41(dq, 1H, J=7.3, 8.6), 4.89(m, 1H), 5.51(m, 1H)

$^{13}$C-NMR (CDCl$_3$): δ 14.03, 22.31, 23.67, 25.98, 37.62, 40.40, 75.42, 118.85, 140.76, 179.70

GC/MS (m/e); 166(M$^+$,), 151, 138, 123, 107, 93, 79, 69, 55, 39, 36

[3] Step F (Recrystallization)

The compound (a) obtained in [2] above (14.7 g; (3S,3aS, 7aR):(3R,3aR,7aS)=90:10) was dissolved in a mixture of heptane (74 ml) and 2-propanol (5 ml), and then allowed to stand at 5° C. After 18 hours, the resulting crystals were collected by filtration to obtain 10.6 g of the purified compound ((3S,3aS,7aR):(3R,3aR,7aS)=99.93:0.07, yield: 72%, optical purity of (3S,3aS,7aR) isomer: 99.86% ee).

$^1$H-NMR (CDCl$_3$): δ 1.26(d, 3H, J=7.3), 1.73(s, 3H), 1.73 (m, 1H), 1.82(m, 1H), 1.97(m, 2H), 2.25(m, 1H), 2.41(dq, 1H, J=7.3, 8.6), 4.89(m, 1H), 5.51(m, 1H)

$^{13}$C-NMR (CDCl$_3$): δ 14.03, 22.31, 23.67, 25.98, 37.62, 40.40, 75.42, 118.85, 140.76, 179.70

GC/MS (m/e); 166(M$^+$,), 151, 138, 123, 107, 93, 79, 69, 55, 39, 36

Melting point: 47-51° C.

INDUSTRIAL APPLICABILITY

According to the present invention, wine lactone, which is useful as a flavor or fragrance compound, or a stereoisomer thereof or a mixture thereof can be produced without using any harmful or expensive reagents and without requiring any extreme reaction conditions such as extremely low or high temperatures. According to a preferred embodiment of the present invention, compounds including wine lactone can be produced in a highly selective manner through simple and safe procedures. The process of the present invention is preferred for use in the production of wine lactone or a stereoisomer thereof or a mixture thereof on an industrial scale.

The invention claimed is:

1. A process for producing a compound represented by formula (a), which is wine lactone or a stereoisomer thereof or a mixture thereof:

[Formula 83]

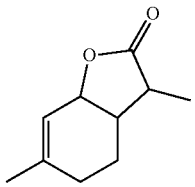

(a)

wherein said process comprises:

A) the step of reacting a β-keto ester represented by formula (1):

[Formula 84]

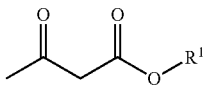

(1)

[wherein R$^1$ is an alkyl group containing 1 to 4 carbon atoms]

with a 2-halo ester represented by formula (2):

[Formula 85]

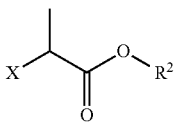

(2)

[wherein R$^2$ is an alkyl group containing 1 to 4 carbon atoms, and X is a chlorine atom or a bromine atom]

under basic conditions to obtain a 2-aceto-3-methyl-succinic acid ester represented by formula (3):

[Formula 86]

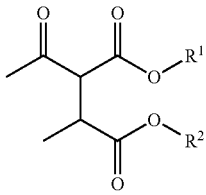

(3)

[wherein R$^1$ is as defined in formula (1), and R$^2$ is as defined in formula (2)];

B-1) the step of reacting the 2-aceto-3-methyl-succinic acid ester obtained in step A) with methyl vinyl ketone under basic conditions, followed by hydrolysis to obtain an α-methyl-γ-keto acid represented by formula (4):

[Formula 87]

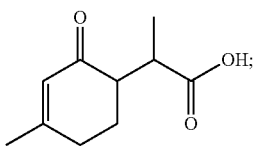

(4)

and

C) the step of reducing the α-methyl-γ-keto acid obtained in step B-1) to obtain the compound represented by formula (a).

2. The process according to claim 1, wherein step C) comprises causing asymmetric reduction reaction in the presence of an optically active form of a ruthenium complex selected from compounds represented by formula (6) or (7) and in the presence of a hydrogen donor:

[Formula 88]

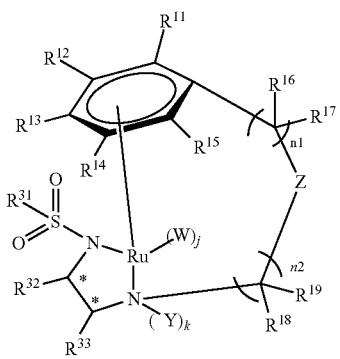

(6)

[wherein * represents an asymmetric carbon atom, $R^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—NR$^{20}$R$^{21}$), a 5- or 6-membered cyclic amino group, an acylamino group (—NH—CO—R$^{20}$), a hydroxyl group, an alkoxy group (—OR$^{20}$), an acyl group (—CO—R$^{20}$), a carboxyl group, an alkoxycarbonyl group (—COOR$^{20}$), a phenoxycarbonyl group, a mercapto group, an alkylthio group (—SR$^{20}$), a silyl group (—SiR$^{20}$R$^{21}$R$^{22}$) and a nitro group (—NO$_2$), wherein R$^{20}$, R$^{21}$ and R$^{22}$ are each independently a hydrogen atom, an alkyl group containing 1 to 10 carbon atoms, or a cycloalkyl group containing 3 to 10 carbon atoms, Y is a hydrogen atom, W is a trifluoromethanesulfonyloxy group, a p-toluenesulfonyloxy group, a methanesulfonyloxy group, a benzenesulfonyloxy group, a hydrogen atom, or a halogen atom, j and k are each independently 0 or 1, provided that j+k is not 1, $R^{32}$ and $R^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, $R^{32}$ and $R^{33}$ may together form a ring, $R^{11}$, $R^{12}$, $R^{13}$, $R^{14}$ and $R^{15}$ each independently represent a hydrogen atom, an alkyl group containing 1 to 10 carbon atoms, or an alkoxy group containing 1 to 10 carbon atoms, $R^{16}$, $R^{17}$, $R^{18}$ and $R^{19}$ are each independently a hydrogen atom, a hydroxyl group, an alkyl group containing 1 to 10 carbon atoms, or an alkoxy group containing 1 to 10 carbon atoms, or alternatively, $R^{16}$ and $R^{17}$ may form a carbonyl group together with their adjacent carbon atom and/or $R^{18}$ and $R^{19}$ may form a carbonyl group together with their adjacent carbon atom, Z is an oxygen atom or a sulfur atom, $n_1$ is 1 or 2, and $n_2$ is an integer of 1 to 3]

[Formula 89]

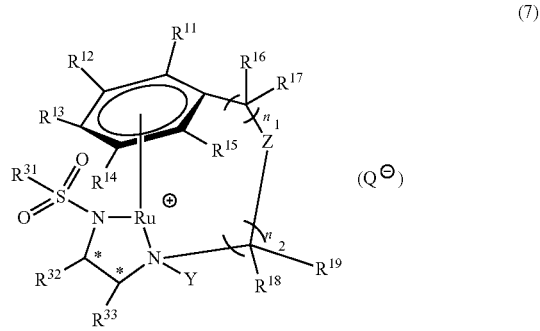

(7)

[wherein * represents an asymmetric carbon atom, $R^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—NR$^{20}$R$^{21}$), a 5- or 6-membered cyclic amino group, an acylamino group (—NH—CO—R$^{20}$), a hydroxyl group, an alkoxy group (—OR$^{20}$), an acyl group (—CO—R$^{20}$), a carboxyl group, an alkoxycarbonyl group (—COOR$^{20}$), a phenoxycarbonyl group, a mercapto group, an alkylthio group (—SR$^{20}$), a silyl group (—SiR$^{20}$R$^{21}$R$^{22}$) and a nitro group (—NO$_2$), $R^{20}$, $R^{21}$ and $R^{22}$ are each independently a hydrogen atom, an alkyl group containing 1 to 10 carbon atoms, or a cycloalkyl group containing 3 to 10 carbon atoms, Y is a hydrogen atom, $R^{32}$ and $R^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, $R^{32}$ and $R^{33}$ may together form a ring, $R^{11}$, $R^{12}$, $R^{13}$, $R^{14}$ and $R^{15}$ are each independently a hydrogen atom, an alkyl group containing 1 to 10 carbon atoms, or an alkoxy group containing 1 to 10 carbon atoms, $R^{16}$, $R^{17}$, $R^{18}$ and $R^{19}$ are each independently a hydrogen atom, a hydroxyl group, an alkyl group containing 1 to 10 carbon atoms, or an alkoxy group containing 1 to 10 carbon atoms, or alternatively, $R^{16}$ and $R^{17}$ may form a carbonyl group together with their adjacent carbon atom and/or $R^{18}$ and $R^{19}$ may form a carbonyl group together with their adjacent carbon atom, Z is an oxygen atom or a sulfur atom, $Q^-$ is a counter anion, $n_1$ is 1 or 2, and $n_2$ is an integer of 1 to 3].

3. The process according to claim 2, wherein the ruthenium complex represented by formula (6) is a compound represented by the following formula:

[Formula 90]

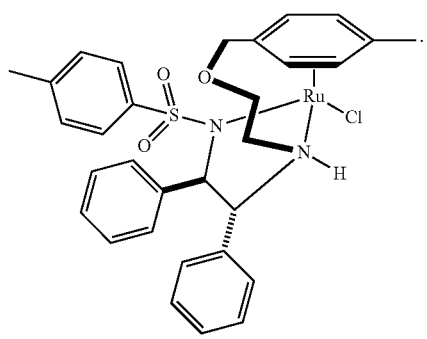

4. The process according to claim 1, which further comprises the step of distilling the compound obtained in step C) under basic conditions to obtain a diastereomeric isomer mixture composed of (3S,3aS,7aR) and (3R,3aR,7aS) isomers represented by the following formulae:

[Formula 91]

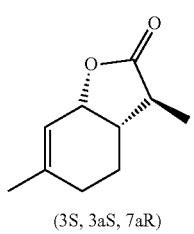

(3S, 3aS, 7aR)

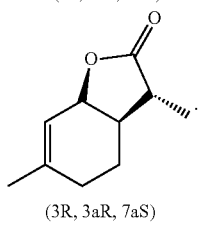

(3R, 3aR, 7aS)

5. The process according to claim 2, which further comprises the step of distilling the compound obtained in step C) under basic conditions to obtain a diastereomeric isomer mixture composed of (3S,3aS,7aR) and (3R,3aR,7aS) isomers represented by the following formulae:

[Formula 92]

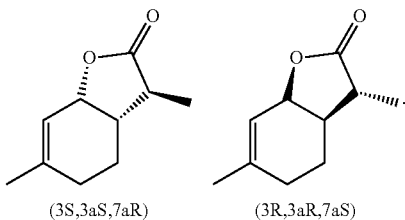

(3S,3aS,7aR)   (3R,3aR,7aS)

6. The process according to claim 5, which further comprises the step of recrystallization to obtain the (3S,3aS,7aR) isomer represented by the following formula:

[Formula 93]

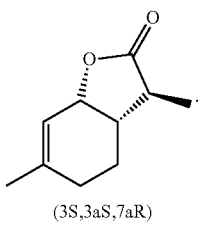

(3S,3aS,7aR)

7. A process for producing a compound represented by formula (a), which is wine lactone or a stereoisomer thereof or a mixture thereof:

[Formula 94]

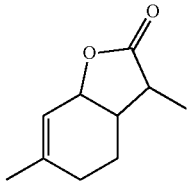

(a)

wherein said process comprises:

A) the step of reacting a β-keto ester represented by formula (1):

[Formula 95]

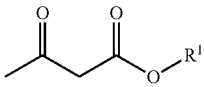

(1)

[wherein $R^1$ is an alkyl group containing 1 to 4 carbon atoms]

with a 2-halo ester represented by formula (2):

[Formula 96]

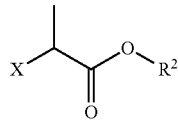

(2)

[wherein $R^2$ is an alkyl group containing 1 to 4 carbon atoms, and X is a chlorine atom or a bromine atom] under basic conditions to obtain a 2-aceto-3-methyl-succinic acid ester represented by formula (3):

[Formula 97]

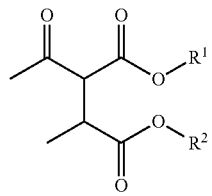

(3)

[wherein $R^1$ is as defined in formula (1), and $R^2$ is as defined in formula (2)];

B-2) the step of reacting the 2-aceto-3-methyl-succinic acid ester obtained in step A) with methyl vinyl ketone under basic conditions, followed by decarboxylation reaction to obtain an α-methyl-γ-keto acid ester represented by formula (5):

[Formula 98]

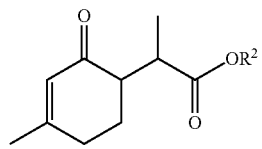

(5)

[wherein $R^2$ is as defined in formula (2)];

B-3) the step of hydrolyzing the α-methyl-γ-keto acid ester obtained in step B-2) to obtain an α-methyl-γ-keto acid represented by formula (4):

[Formula 99]

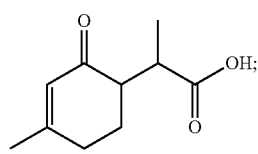

(4)

and

C) the step of reducing the α-methyl-γ-keto acid obtained in step B-3) to obtain the compound represented by formula (a).

8. The process according to claim 7, wherein step C) comprises causing asymmetric reduction reaction in the presence of an optically active form of a ruthenium complex selected from compounds represented by formula (6) or (7) and in the presence of a hydrogen donor:

[Formula 100]

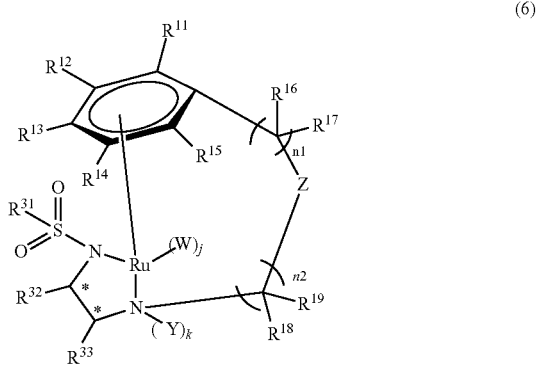

(6)

[wherein * represents an asymmetric carbon atom, $R^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—$NR^{20}R^{21}$), a 5- or 6-membered cyclic amino group, an acylamino group (—NH—CO—$R^{20}$), a hydroxyl group, an alkoxy group (—$OR^{20}$), an acyl group (—CO—$R^{20}$), a carboxyl group, an alkoxycarbonyl group (—$COOR^{20}$), a phenoxycarbonyl group, a mercapto group, an alkylthio group (—$SR^{20}$), a silyl group (—$SiR^{20}R^{21}R^{22}$) and a nitro group (—$NO_2$), wherein $R^{20}$, $R^{21}$ and $R^{22}$ are each independently a hydrogen atom, an alkyl group containing 1 to 10 carbon atoms, or a cycloalkyl group containing 3 to 10 carbon atoms, Y is a hydrogen atom, W is a trifluoromethanesulfonyloxy group, a p-toluenesulfonyloxy group, a methanesulfonyloxy group, a benzenesulfonyloxy group, a hydrogen atom, or a halogen atom, j and k are each independently 0 or 1, provided that j+k is not 1, $R^{32}$ and $R^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, $R^{32}$ and $R^{33}$ may together form a ring, $R^{11}$, $R^{12}$, $R^{13}$, $R^{14}$ and $R^{15}$ each independently represent a hydrogen atom, an alkyl group containing 1 to 10 carbon atoms, or an alkoxy group containing 1 to 10 carbon atoms, R$^{16}$, R$^{17}$, R$^{18}$ and R$^{19}$ are each independently a hydrogen atom, a hydroxyl group, an alkyl group containing 1 to 10 carbon atoms, or an alkoxy group containing 1 to 10 carbon atoms, or alternatively, R$^{16}$ and R$^{17}$ may form a carbonyl group together with their adjacent carbon atom and/or R$^{18}$ and R$^{19}$ may form a carbonyl group together with their adjacent carbon atom, Z is an oxygen atom or a sulfur atom, n$_1$ is 1 or 2, and n$_2$ is an integer of 1 to 3]

[Formula 101]

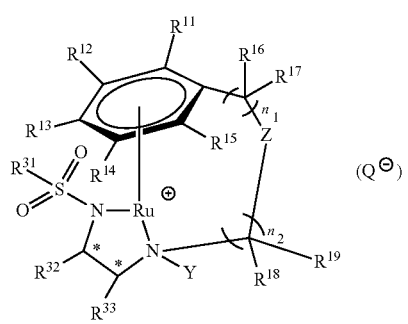

(7)

(Q$^{\ominus}$)

[wherein * represents an asymmetric carbon atom,
R$^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—NR$^{20}$R$^{21}$), a 5- or 6-membered cyclic amino group, an acylamino group (—NH—CO—R$^{20}$), a hydroxyl group, an alkoxy group (—OR$^{20}$), an acyl group (—CO—R$^{20}$), a carboxyl group, an alkoxycarbonyl group (—COOR$^{20}$), a phenoxycarbonyl group, a mercapto group, an alkylthio group (—SR$^{20}$), a silyl group (—SiR$^{20}$R$^{21}$R$^{22}$) and a nitro group (—NO$_2$), R$^{20}$, R$^{21}$ and R$^{22}$ are each independently a hydrogen atom, an alkyl group containing 1 to 10 carbon atoms, or a cycloalkyl group containing 3 to 10 carbon atoms, Y is a hydrogen atom, R$^{32}$ and R$^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, R$^{32}$ and R$^{33}$ may together form a ring, R$^{11}$, R$^{12}$, R$^{13}$, R$^{14}$ and R$^{15}$ are each independently a hydrogen atom, an alkyl group containing 1 to 10 carbon atoms, or an alkoxy group containing 1 to 10 carbon atoms, R$^{16}$, R$^{17}$, R$^{18}$ and R$^{19}$ are each independently a hydrogen atom, a hydroxyl group, an alkyl group containing 1 to 10 carbon atoms, or an alkoxy group containing 1 to 10 carbon atoms, or alternatively, R$^{16}$ and R$^{17}$ may form a carbonyl group together with their adjacent carbon atom and/or R$^{18}$ and R$^{19}$ may form a carbonyl group together with their adjacent carbon atom, Z is an oxygen atom or a sulfur atom, Q$^-$ is a counter anion, n$_1$ is 1 or 2, and n$_2$ is an integer of 1 to 3].

9. The process according to claim 8, wherein the ruthenium complex represented by formula (6) is a compound represented by the following formula:

[Formula 102]

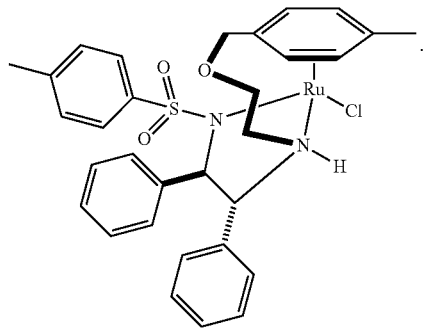

10. The process according to claim 7, which further comprises the step of distilling the compound obtained in step C) under basic conditions to obtain a diastereomeric isomer mixture composed of (3S,3aS,7aR) and (3R,3aR,7aS) isomers represented by the following formulae:

[Formula 103]

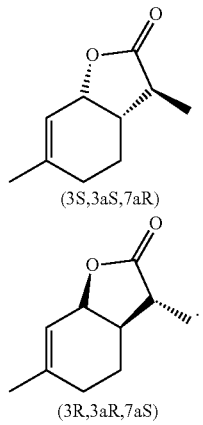

(3S,3aS,7aR)

(3R,3aR,7aS)

11. The process according to claim 8, which further comprises the step of distilling the compound obtained in step C) under basic conditions to obtain a diastereomeric isomer mixture composed of (3S,3aS,7aR) and (3R,3aR,7aS) isomers represented by the following formulae:

[Formula 104]

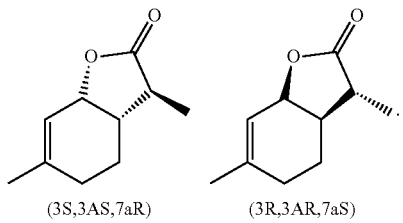

(3S,3AS,7aR)    (3R,3AR,7aS)

12. The process according to claim 11, which further comprises the step of recrystallization to obtain the (3S,3aS,7aR) isomer represented by the following formula:

[Formula 105]

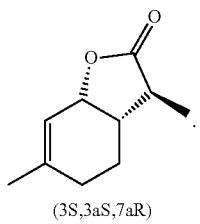

(3S,3aS,7aR)

13. A process for producing a compound represented by formula (a), which is wine lactone or a stereoisomer thereof or a mixture thereof:

[Formula 106]

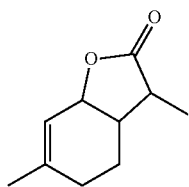

(a)

wherein said process comprises:
A) the step of reacting a β-keto ester represented by formula (1):

[Formula 107]

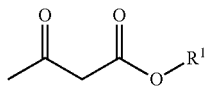

(1)

[wherein $R^1$ is an alkyl group containing 1 to 4 carbon atoms]
with a 2-halo ester represented by formula (2):

[Formula 108]

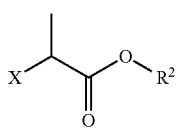

(2)

[wherein $R^2$ is an alkyl group containing 1 to 4 carbon atoms, and X is a chlorine atom or a bromine atom] under basic conditions to obtain a 2-aceto-3-methyl-succinic acid ester represented by formula (3):

[Formula 109]

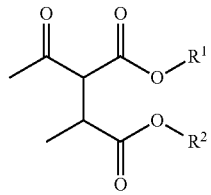

(3)

[wherein $R^1$ is as defined in formula (1), and $R^2$ is as defined in formula (2)];
B-2) the step of reacting the 2-aceto-3-methyl-succinic acid ester obtained in step A) with methyl vinyl ketone under basic conditions, followed by decarboxylation reaction to obtain an α-methyl-γ-keto acid ester represented by formula (5):

[Formula 110]

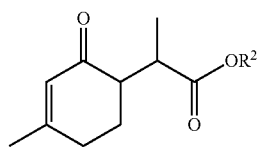

(5)

[wherein $R^2$ is as defined in formula (2)]; and
E) the step of reducing the α-methyl-γ-keto acid ester obtained in step B-2) in the presence of a ruthenium complex selected from compounds represented by formula (6) or (7) and in the presence of a hydrogen donor to obtain the compound represented by formula (a):

[Formula 111]

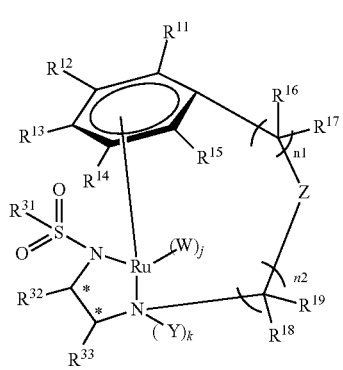

(6)

[wherein * represents an asymmetric carbon atom,
$R^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—NR$^{20}$R$^{21}$), a 5- or 6-membered cyclic amino group, an acylamino group (—NH—CO—R$^{20}$), a hydroxyl group, an alkoxy group (—OR$^{20}$), an acyl group (—CO—R$^{20}$), a carboxyl group, an alkoxycarbonyl group (—COOR$^{20}$), a phenoxycarbonyl group, a mercapto group, an alkylthio group (—SR$^{20}$), a silyl group (—SiR$^{20}$R$^{21}$R$^{22}$) and a nitro group (—NO$_2$), wherein R$^{20}$, R$^{21}$ and R$^{22}$ are each independently a hydrogen atom, an alkyl group containing 1 to 10 carbon atoms, or a cycloalkyl group containing 3 to 10 carbon atoms, Y is a hydrogen atom, W is a trifluoromethanesulfonyloxy group, a p-toluenesulfonyloxy group, a methanesulfonyloxy group, a benzenesulfonyloxy group, a hydrogen atom, or a halogen atom, j and k are each independently 0 or 1, provided that j+k is not 1, R$^{32}$ and R$^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, R$^{32}$ and R$^{33}$ may together form a ring, R$^{11}$, R$^{12}$, R$^{13}$, R$^{14}$ and R$^{15}$ each independently represent a hydrogen atom, an alkyl group containing 1 to 10 carbon atoms, or an alkoxy group containing 1 to 10 carbon atoms, R$^{16}$, R$^{17}$, R$^{18}$ and R$^{19}$ are each independently a hydrogen atom, a hydroxyl group, an alkyl group containing 1 to 10 carbon atoms, or an alkoxy group containing 1 to 10 carbon atoms, or alternatively, R$^{16}$ and R$^{17}$ may form a carbonyl group together with their adjacent carbon atom and/or R$^{18}$ and R$^{19}$ may form a carbonyl group together with their adjacent carbon atom, Z is an oxygen atom or a sulfur atom, $n_1$ is 1 or 2, and $n_2$ is an integer of 1 to 3]

[Formula 112]

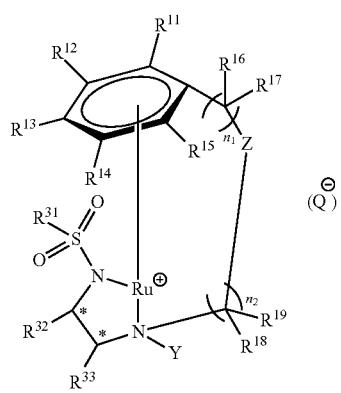

[wherein * represents an asymmetric carbon atom,

R$^{31}$ is an alkyl group containing 1 to 10 carbon atoms; a halogenated alkyl group containing 1 to 10 carbon atoms; a 10-camphoryl group; an amino group which may be substituted with one or two alkyl groups each containing 1 to 10 carbon atoms; or an aryl group which may be substituted with at least one substituent selected from the group consisting of an alkyl group containing 1 to 10 carbon atoms, a halogenated alkyl group containing 1 to 10 carbon atoms, a halogen atom, a cyano group (—CN), an amino group, an alkylamino group (—NR$^{20}$R$^{21}$), a 5- or 6-membered cyclic amino group, an acylamino group (—NH—CO—R$^{20}$), a hydroxyl group, an alkoxy group (—OR$^{20}$), an acyl group (—CO—R$^{20}$), a carboxyl group, an alkoxycarbonyl group (—COOR$^{20}$), a phenoxycarbonyl group, a mercapto group, an alkylthio group (—SR$^{20}$), a silyl group (—SiR$^{20}$R$^{21}$R$^{22}$) and a nitro group (—NO$_2$), R$^{20}$, R$^{21}$ and R$^{22}$ are each independently a hydrogen atom, an alkyl group containing 1 to 10 carbon atoms, or a cycloalkyl group containing 3 to 10 carbon atoms, Y is a hydrogen atom, R$^{32}$ and R$^{33}$ are each independently a hydrogen atom; an alkyl group containing 1 to 10 carbon atoms; a phenyl group which may be substituted with at least one substituent selected from the group consisting of an alkyl group containing 1 to 10 carbon atoms, an alkoxy group containing 1 to 10 carbon atoms and a halogen atom; or a cycloalkyl group containing 3 to 8 carbon atoms, or alternatively, R$^{32}$ and R$^{33}$ may together form a ring, R$^{11}$, R$^{12}$, R$^{13}$, R$^{14}$ and R$^{15}$ are each independently a hydrogen atom, an alkyl group containing 1 to 10 carbon atoms, or an alkoxy group containing 1 to 10 carbon atoms, R$^{16}$, R$^{17}$, R$^{18}$ and R$^{19}$ are each independently a hydrogen atom, a hydroxyl group, an alkyl group containing 1 to 10 carbon atoms, or an alkoxy group containing 1 to 10 carbon atoms, or alternatively, R$^{16}$ and R$^{17}$ may form a carbonyl group together with their adjacent carbon atom and/or R$^{18}$ and R$^{19}$ may form a carbonyl group together with their adjacent carbon atom, Z is an oxygen atom or a sulfur atom, Q$^-$ is a counter anion, $n_1$ is 1 or 2, and $n_2$ is an integer of 1 to 3].

14. The process according to claim 9, wherein in step E), the ruthenium complex selected from compounds represented by formula (6) or (7) is an optically active ruthenium complex and is used to cause asymmetric reduction reaction.

15. The process according to claim 13, wherein the ruthenium complex represented by formula (6) is a compound represented by the following formula:

[Formula 113]

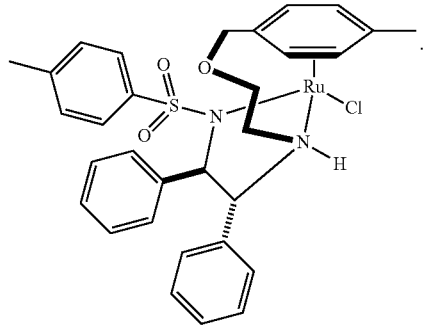

16. The process according to claim 13, which further comprises the step of distilling the compound obtained in step E) under basic conditions to obtain a diastereomeric isomer mixture composed of (3S,3aS,7aR) and (3R,3aR,7aS) isomers represented by the following formulae:

[Formula 114]

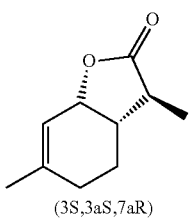

(3S,3aS,7aR)

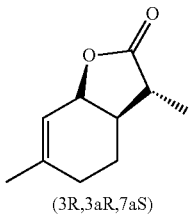

(3R,3aR,7aS)

17. The process according to claim 16, which further comprises the step of recrystallization to obtain the (3S,3aS,7aR) isomer represented by the following formula:

[Formula 115]

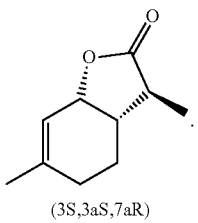

(3S,3aS,7aR)

18. A process for producing a compound represented by formula (a), which is wine lactone or a stereoisomer thereof or a mixture thereof:

[Formula 116]

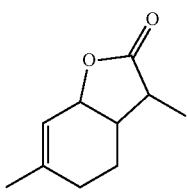

(a)

wherein said process comprises:

A) the step of reacting a β-keto ester represented by formula (1):

[Formula 117]

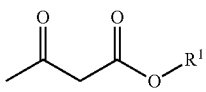

(1)

[wherein R¹ is an alkyl group containing 1 to 4 carbon atoms]

with a 2-halo ester represented by formula (2):

[Formula 118]

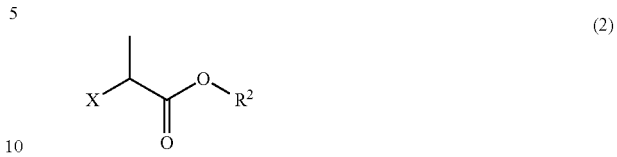

(2)

[wherein R² is an alkyl group containing 1 to 4 carbon atoms, and X is a chlorine atom or a bromine atom]

under basic conditions to obtain a 2-aceto-3-methyl-succinic acid ester represented by formula (3):

[Formula 119]

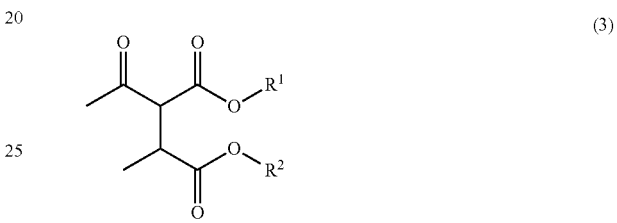

(3)

[wherein R¹ is as defined in formula (1), and R² is as defined in formula (2)];

B-2) the step of reacting the 2-aceto-3-methyl-succinic acid ester obtained in step A) with methyl vinyl ketone under basic conditions, followed by decarboxylation reaction to obtain an α-methyl-γ-keto acid ester represented by formula (5):

[Formula 120]

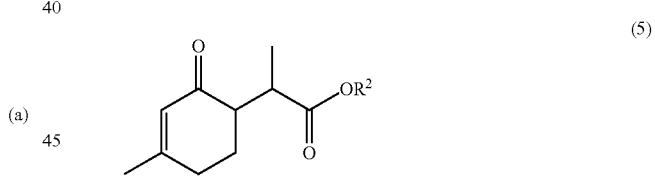

(5)

[wherein R² is as defined in formula (2)]; and

E) the step of subjecting the α-methyl-γ-keto acid ester obtained in step B-2) to asymmetric hydrogenation reaction under basic conditions and in the presence of an optically active ruthenium complex represented by formula (8) and a hydrogen gas to obtain the compound represented by formula (a):

[Formula 121]

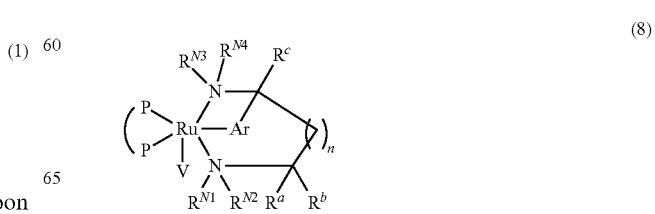

(8)

[wherein p⌒p represents an optically active diphosphine,

V is an anionic group, $R^a$, $R^b$ and $R^c$ are each independently a hydrogen atom, an optionally substituted $C_1$ to $C_{20}$ alkyl group, an optionally substituted $C_2$ to $C_{20}$ alkenyl group, an optionally substituted $C_3$ to $C_8$ cycloalkyl group, an optionally substituted $C_7$ to $C_{20}$ aralkyl group, an optionally substituted aryl group, or an optionally substituted heterocyclyl group, or alternatively, $R^b$ and $R^c$ may together form an alkylene group or an alkylenedioxy group, $R^{N1}$, $R^{N2}$, $R^{N3}$ and $R^{N4}$ are each independently a hydrogen atom, an optionally substituted $C_1$ to $C_{20}$ alkyl group, an optionally substituted $C_2$ to $C_{20}$ alkenyl group, an optionally substituted $C_7$ to $C_{20}$ aralkyl group, or an optionally substituted $C_3$ to $C_8$ cycloalkyl group, provided that at least one of $R^{N1}$, $R^{N2}$, $R^{N3}$ and $R^{N4}$ is a hydrogen atom, and $R^{N1}$ and $R^a$ may together form an alkylene group, n is an integer of 0 to 3, and Ar is an optionally substituted arylene group].

19. The process according to claim 18, wherein the optically active ruthenium complex of formula (8) is a compound represented by the following formula:

[Formula 122]

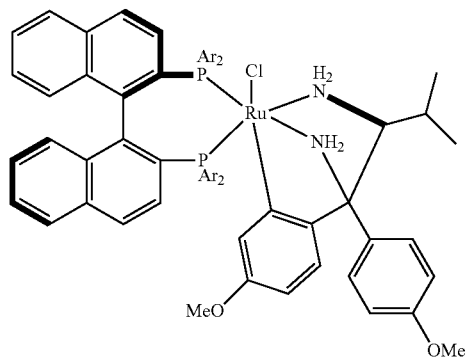

Ar:

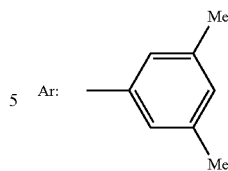

[wherein Me represents a methyl group].

20. The process according to claim 18, which further comprises the step of distilling the compound obtained in step E) under basic conditions to obtain a diastereomeric isomer mixture composed of (3S,3aS,7aR) and (3R,3aR,7aS) isomers represented by the following formulae:

[Formula 123]

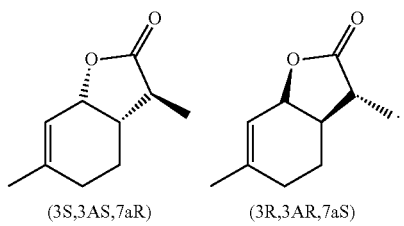

(3S,3AS,7aR)     (3R,3AR,7aS)

21. The process according to claim 20, which further comprises the step of recrystallization to obtain the (3S,3aS,7aR) isomer represented by the following formula:

[Formula 124]

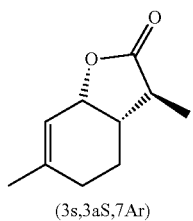

(3s,3aS,7Ar)

* * * * *